United States Patent
Lee-Sepsick et al.

(10) Patent No.: US 9,788,820 B2
(45) Date of Patent: Oct. 17, 2017

(54) METHODS AND DEVICES FOR CERVICAL CELL AND TISSUE SAMPLING

(71) Applicant: FEMASYS INC, Suwanee, GA (US)

(72) Inventors: Kathy Lee-Sepsick, Suwanee, GA (US); Max S. Azevedo, Alpharetta, GA (US); Jeffrey A. Marcus, Atlanta, GA (US)

(73) Assignee: FEMASYS INC, Suwanee, GA (US)

( * ) Notice: Subject to any disclaimer, the term of this patent is extended or adjusted under 35 U.S.C. 154(b) by 167 days.

(21) Appl. No.: 13/670,322

(22) Filed: Nov. 6, 2012

(65) Prior Publication Data
US 2013/0158429 A1    Jun. 20, 2013

Related U.S. Application Data

(60) Provisional application No. 61/570,863, filed on Dec. 15, 2011.

(51) Int. Cl.
*A61B 10/04*    (2006.01)
*A61B 5/00*    (2006.01)
(Continued)

(52) U.S. Cl.
CPC ............ *A61B 10/04* (2013.01); *A61B 5/4331* (2013.01); *A61B 10/0275* (2013.01);
(Continued)

(58) Field of Classification Search
CPC .............................. A61B 10/04; A61B 10/0291
See application file for complete search history.

(56) References Cited

U.S. PATENT DOCUMENTS

| 1,719,428 A | 7/1929 | Friedman |
| 3,400,708 A | 9/1968 | Scheidt |
| (Continued) | | |

FOREIGN PATENT DOCUMENTS

| BR | 3020120055326.0 | 10/2012 |
| CA | 148113 | 10/2012 |
| (Continued) | | |

OTHER PUBLICATIONS

U.S. Appl. No. 61/570,863, filed Dec. 15, 2011, K. Lee-Sepsick.
(Continued)

*Primary Examiner* — Daniel Cerioni
*Assistant Examiner* — Yasmeen S Warsi
(74) *Attorney, Agent, or Firm* — Morris Manning & Martin LLP

(57) ABSTRACT

The present invention comprises methods and devices comprising a cutting element used to contact circumferentially and longitudinally the surface walls of the endocervical canal to provide for broad and complete contact of the intended surface with the device, resulting in attainment of a sufficient volume and comprehensive tissue sample for analysis as an endocervical curettage or screening pap smear. The device may provide for a reservoir for the obtained sample to be contained when removing from the cervical canal and vagina. The device may be comprised of a detachable means or be of a material that allows the user to cut the sampling head of the device for placement in collection means to maximize the amount of tissue or cells being sent to the laboratory for analysis.

10 Claims, 8 Drawing Sheets

(51) Int. Cl.
    *A61B 10/02*     (2006.01)
    *A61B 17/3207*     (2006.01)

(52) U.S. Cl.
    CPC .. *A61B 10/0291* (2013.01); *A61B 17/320725* (2013.01); *A61B 2017/320733* (2013.01)

(56) References Cited

U.S. PATENT DOCUMENTS

| | | | | |
|---|---|---|---|---|
| 4,318,414 | A * | 3/1982 | Schuster | A61B 10/0291 600/572 |
| 5,456,265 | A | 10/1995 | Yim | 128/756 |
| 6,336,905 | B1 | 1/2002 | Colaianni | 600/569 |
| 2002/0087096 | A1 * | 7/2002 | Anderson et al. | 600/572 |
| 2009/0131819 | A1 | 5/2009 | Ritchie et al. | |

FOREIGN PATENT DOCUMENTS

| | | |
|---|---|---|
| CA | 148113.0 | 10/2012 |
| CA | 2859403 | 6/2014 |
| CN | 1440255 A | 9/2003 |
| CN | 101147059 A | 3/2008 |
| CN | 101502426 A | 8/2009 |
| CN | 101687067 | 3/2010 |
| CN | 20120507185.7 | 10/2012 |
| CN | 201230507185.7 | 10/2012 |
| CN | 201280068606.8 | 12/2012 |
| CN | 104394775 A | 3/2015 |
| EP | 001349013-0001 | 10/2012 |
| EP | 12857042.1 | 12/2012 |
| EP | 2790589 A1 | 10/2014 |
| HK | 1202161.6 | 10/2012 |
| IN | 248965.0 | 10/2012 |
| IN | 5898/DELNP/2014 | 12/2012 |
| JP | 2012-025697 | 10/2012 |
| JP | 2014-547514 | 12/2012 |
| JP | 1476736 | 7/2013 |
| KR | 30-2012-0050431 | 10/2012 |
| KR | 2014-7019269 | 12/2012 |
| KR | 20140103148 A | 8/2014 |
| WO | WO 01/01867 A1 | 1/2001 |
| WO | WO 01/62157 A1 | 8/2001 |
| WO | WO-2006/104333 A1 | 10/2006 |
| WO | WO-2008/103839 A2 | 8/2008 |
| WO | PCT/US2012/069886 | 12/2012 |
| WO | WO 2013/090807 | 6/2013 |

OTHER PUBLICATIONS

U.S. Appl. No. 29/418,924, filed Apr. 23, 2012, K. Lee-Sepsick.
U.S. Appl. No. 29/418,924, filed Apr. 23, 2012, K Lee-Sepsick.
International Search Report and Written Opinion dated Feb. 25, 2012 for International Application No. PCT/2012/069886 filed Dec. 14, 2011 and published as WO 2013/090807 dated Jun. 20, 2013 (Inventors—Kathy Lee-Sepsick, et al. // Applicant—Femasys Inc). (8 pages).
Abu J, et al. (2005) Endocervical curettage at the time of colposcopic assessment of the uterine cervix. Obstet Gynecol Surv. 60(5): 315-320.
Andersen W, et al. (1988) Sensitivity and specificity of endocervical curettage and the endocervical brush for the evaluation of the endocervical canal. Am J Obstet Gyncol. 159(3):702-707.
ASCCP (American Society for Colposcopy and Cervical Pathology). Practice Management, Colposcopy: Basic components of the colposcopic exam (Step 12). http://www.asccp.org/PracticeManagement/Cervix/Colposcopy, Aug. 2012.
Bidus M, et al. (2005) The clinical utility of the diagnostic endocervical curettage. Clin Obstet Gynecol. 45(1): 202-208.
Boardman LA, et al. (2003) A randomized trial of the sleeved cytobrush and the endocervical curette. Obstet Gynecol. 101(3): 426-430.
Driggers RW, et al. (2008) To ECC or not to ECC: the question remains. Obstet Gyncol Clin N Am. 35(4): 583-597.
Gage JC, et al. (2006) Number of cervical biopsies and sensitivity of colposcopy. Obstet Gynecol. 108(2): 264-272.
Gosewehr JA, et al. (1991) Improving the Cytobrush as an aid in the evaluation of the abnormal Papanicolaou test. Obstet Gynecol. 78(3 Pt 1): 440-443.
Helmerhorst TJ. (1992) Clinical significance of endocervical curettage as part of colposcopic evaluation. A review. Int J Gynecol Cancer. 2(5): 256-262.
Klam S, et al. Comparison of endocervical curettage and endocervical brushing. Obstet Gynecol. 96(1): 90-94.
Koss LG. (1989) The Papanicolaou test for cervical cancer detection. A triumph and a tragedy. JAMA. 261(5):737-743.
Moniak C, et al. (2000) Endocervical curettage in evaluating abnormal cervical cytology. J Reprod Med. 45(4): 285-292.
National Cancer Institute's SEER Stat Fact Sheets. Cancer: Cervix Uteri. Surveillance Epidemiology and End Results. Available at http://seer.cancer.gov/statfacts/html/cervix.html (4 pages).
Pretorius RG, et al. (2004) Colposcopically directed biopsy, random cervical biopsy, and endocervical curettage in the diagnosis of cervical intraepithelial neoplasia II or worse. Am J Obstet Gynecol. 191(2): 430-434.
Saslow D, et al. (2012) American Cancer Society, American Society for Colposcopy and Cervical Pathology, and American Society for Clinical Pathology screening guidelines for the prevention and early detection of cervical cancer. J Lower Genital Tract Dis. 16(3): 175-204.
Saslow D, et al. (2012) American Cancer Society, American Society for Colposcopy and Cervical Pathology, and American Society for Clinical Pathology screening guidelines for the prevention and early detection of cervical cancer. CA Cancer J Clin. 62(3): 147-172.
Schiffman M, et al. (2010) From human papillomavirus to cervical cancer. Obstet Gynecol. 116(1): 177-185.
Schiffman M, et al. (2007) Human papillomavirus and cervical cancer. Lancet. 370(9590): 890-907.
Solomon D, et al., (2007) Diagnostic utility of endocervical curettage in women undergoing colposcopy for equivocal or low-grade colposcopy cytologic abnormalities. Obstet Gynecol. 110(2 Pt. 1): 288-295.
Wright TC, et al. (2007) 2006 consensus guidelines for the management of women with abnormal cervical screening tests (by ASCCP). J Lower Genital Tract Dis. 11(4): 201-222.
Supplementary European Search Report dated Jun. 25, 2015 by the European Patent Office for European Patent Application No. 12857042.1, which was filed on Dec. 14, 2012 and published as 2790589 on Oct. 22, 2014 (Inventor—Lee-Sepsick et al.; Applicant—Femasys, LLC) (7 pages).
International Preliminary Report on Patentability dated Jun. 17, 2014 by the International Searching Authority for International Patent Application No. PCT/US2012/069886, which was filed on Dec. 14, 2012 and published as WO 2013/090807 on Jun. 20, 2013 (Inventor—Lee-Sepsick et al.; Applicant—Femasys, LLC) (6 pages).
First Office Action issued by the State Intellectual Property Office of the People's Republic of China dated Nov. 24, 2015 for application 201280068606.8, filed on Dec. 14, 2012 and published as CN 104394775 on Mar. 4, 2014 (Applicant—Femasys, Inc. // Inventor—Lee-Sepsick, et al.) (Original 9 pages // Translation 7 pages).

* cited by examiner

METHODS AND DEVICES FOR CERVICAL CELL AND TISSUE SAMPLING

RELATED APPLICATIONS

The present application claims the priority of U.S. Provisional Patent Application Ser. No. 61/570,863, filed Dec. 15, 2011, which is herein incorporated in its entirety.

TECHNICAL FIELD

The present invention relates to methods and devices for obtaining samples simultaneously or sequentially of the endocervical cells.

BACKGROUND

Current methods of sampling the endocervix for cells are inadequate and may be harmful to the anatomy of a patient. What is needed are methods and devices that can obtain a more complete sampling of the area without degradation of the anatomical area.

SUMMARY

The present invention comprises methods and devices for sampling cervical tissues, for example, sampling the endocervical canal for analysis as an endocervical curettage or pap smear procedure. The methods and devices may comprise scraping the canal to obtain an adequate sample. The present invention comprises sampling devices and methods that are improved over currently available devices in the quantity of tissue and cells obtained, the protection of the sample once it is obtained, and the ability to completely sample the target area, such as the transformation zone, as the target area is assessed circumferentially, and to provide methods using devices disclosed herein for minimal contamination of the sample once it is acquired and the device is removed from the patient. Methods and devices disclosed herein also offer improved patient care in that there is minimal patient pain and discomfort in the use of the disclosed devices. The invention disclosed herein provides methods and devices that decrease patient discomfort, for example, during an endocervical curettage (ECC) procedure, and devices that sample the target area to provide accurate and sensitive detection of cervical abnormalities. Aspects of the present invention aid in providing a more patient-oriented device that is more comfortable and causes less pain to the patient than currently used devices. For example, a method of the present invention comprises collecting a sample of tissue and cells from the endocervix by insertion of the device only one time into the patient's endocervix. Currently used devices often require more than one insertion of the device into the endocervix to obtain adequate samples. A device of the present invention comprises a sample collection area and wand that are cylindrical in shape which is more complementary to the endocervical anatomy than are currently used devices having a rectangularly shaped sample collection device with sharp hard corners contacting the endocervix inner surfaces. Additionally, a device of the present invention may comprise an atraumatic tip or a tapered distal tip of the wand that allows for ease of entry of the device into the endocervical canal. The tip may provide a dilation function to aid in insertion of the device into the endocervical canal.

A device of the present invention comprises handle, a wand surrounded by a sheath, tissue sampling elements, and a sample collection cavity. The device is used for tissue and cell sampling. The device handle remains outside of the patient while the sample collection cavity and tissue sampling elements are placed in proximity to the target area. A target area may be an endocervical surface, for example, the interior surface of the endocervix. The wand is an elongated body, which may be tubular or solid, which is designed to traverse along the entire length or partial length of the inner circumference of the sheath. In embodiments presented herein, the wand is connected to a handle for manipulation of the entire device and the handle may incorporate components to expand the sampling area, comprising tissue sampling elements and a sample collection cavity to allow for scraping of the target area, such as the endocervix, both circumferentially and longitudinally, against the inner surface of the cervical canal to obtain tissue or cells. The sheath of a device of the present invention may be an elongated tubular body designed to allow for an inner shaft to traverse the sheath's inner circumference. The sheath may function to protect the tissue sample from contamination, and may provide the tissue sampling elements by which the sampling is achieved (i.e. serves to scrape the cervical canal), protect the sample from being lost during retraction of the device through the cervical os, and/or aid in device placement. The sampling area comprises the portion of the device where the tissue sampling elements, such as opposing edges of a slit are used as scraping edge(s), are located. The sampling area provides for capturing the tissue and cervical cells located in the endocervical canal.

DESCRIPTION OF FIGURES

The accompanying figures, which are incorporated in and constitute a part of this specification, illustrate several aspects and together with the description serve to explain the principles of the invention.

Figure 1:
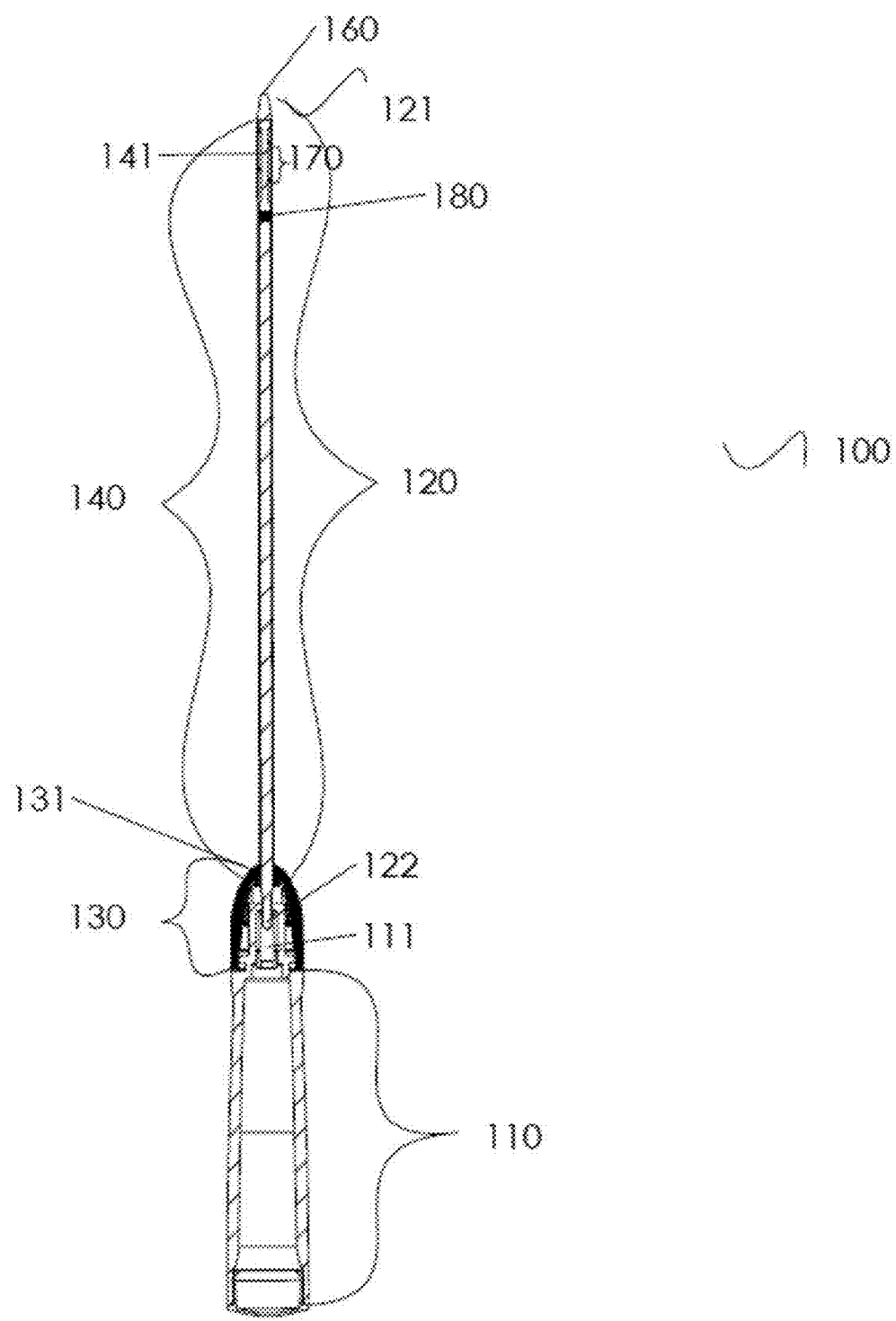
FIG. 1 shows an exemplary example of a device of the present invention.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Detailed Description

The present invention comprises methods and devices for cell sampling. The present invention provides for collection of cell and tissue samples from the area of interest within the cervical canal by having an expandable aspect which allows for substantially complete contact circumferentially to the inner surface of the walls of the cervical canal, with capture of a sufficient sample volume for analysis and minimal contamination of the sample collected. The diagnosis of pre-malignancy and malignancy is dependent on the quantity and complete representation of the targeted area with the purest sample obtained. Obtaining an adequate sample is uncomfortable and usually painful, as the customary available devices require multiple entries to achieve a representative or complete sample. The present invention allows the user to obtain a complete, representative and less contaminated sample from a patient with one or a few entries and removals from the patient.

An aspect of the present invention comprises an expandable sampling area comprising a slit with opposing edges which form a tissue sampling element and a sample collection cavity. A tissue sampling element may comprise opposing edges of a slit. Providing a device having an expanding sampling area provides for the insertion of the device and the collection of the sample to occur substantially along one plane or a single line of entry into the patient. Once inserted, a device of the present invention may be rotated around the single line of entry to collect a sample circumferentially and/or may be moved longitudinally in a distal to proximal direction or proximal to distal direction to collect a sample. A method of using a device of the present invention comprises insertion of the device and collection of the sample along a single plane or a single line of entry into the patient, wherein the rotation occurs in a fixed location with a very small to no rotational diameter of the wand and handle. In collecting a sample using currently available devices, not one of the present invention, a device end having a sampling area is inserted into a patient and then the sampling area is moved within the endocervical canal by the device, such as the insertion member and handle, being rotated through a large arc or circle to apply pressure to the sampling area. The rotation of the insertion member and the handle is not around a single line of entry, but comprises a large rotational area that comprises a large rotational diameter, and resembles a geometric cone with the sampling area at the apex of the cone and the large rotational diameter due to movement of the handle at the base of the cone.

The small to no rotational diameter of a device of the present invention is due to the expandable nature of the tissue sampling elements of a device of the present invention. Before insertion of a device of the present invention into a patient, a tissue sampling element comprising opposing edges of a slit, the opposing edges are adjacent and are aligned with the outer surface of the sheath, which is referred to herein as the closed position. In the closed position, the entire sheath has a substantially uniform diameter from the proximal end to the distal end of the sheath. In use, once the sampling area of the device is in place in the endocervical canal, the slit (or slits) is opened, exposing the opposed edges of a slit and creating the tissue sampling element of the device. This is the open position. There is no need to rotate the entire device in geometric cone-shaped rotation because the expanded sampling area comprising the tissue sampling element contacts the inner surface of the endocervical canal when in the expanded or open position. The opposed edges of the slit or slits are then rotated with a small to no rotational diameter along the single line of entry and because the expanded opposed edges of the slit or slits are in contact with the inner surface of the endocervical canal, the sample is scraped or cut from the inner surface by the opposing edges and collected within the sample collection cavity. Once the sample is within the sample collection cavity, the slit or slits are moved to the closed position, so that the opposing edges are substantially adjacent to each other and the sample collection cavity is substantially covered or closed so that none of the sample within the sample collection cavity can exit and no cellular material or contaminants from outside the sample collection cavity can enter the cavity, which prevents contamination of the sample. As used herein, the sampling area may be said to be expanded or open or in the open position when the opposing edges of the slit are moved apart, as the diameter of the sheath measured at the location of the slit is larger than the diameter of the sheath at a more proximal location where there is no slit. As used herein, the tissue sampling element may be said to be expanded or open or in the open position when the opposing edges of the slit which make up the tissue sampling element are moved apart from each other, as the diameter of the sheath measured at the location of the slit is larger than the diameter of the sheath at a more proximal location where there is no slit. In the closed position, the sampling area and/or the tissue sampling element have substantially the same sheath diameter as the diameter of the sheath where no slit is present.

Having an expandable tissue sampling element also provides more comfort for the patient than currently available devices. The external cervical os has a smaller diameter than the diameter of the endocervical canal. For a currently available device, which does not have an expandable scraping element, the scraping element must be small enough to go through the external cervical os. Then, when in place in the larger diameter endocervical canal, the scraping element or tissue sampling element of the device must be forced against the inner surface of the endocervical canal by rotation of the handle end of the device in a large diameter rotation, forming a geometric cone shape by the rotation of the handle at the base end and the scraping element at the apex while located in the endocervical canal. This type of rotation forces the cervical os to be stretched and forced out of shape, which is at least uncomfortable and generally painful for a patient. Additionally, the currently used devices cannot reliably obtain a sample that comprises tissue and/or cells from a complete transit of a circumferential area of the endocervix. The present invention comprises methods and devices for obtaining a sample of endocervical tissue and/or cells that is a representative sample of the target area, for example, by obtaining a sample from a complete transit of a circumferential area of the endocervix or from a longitudinal path in the endocervix.

A method of the present invention comprises obtaining a sample of the endocervical canal using a device comprising a sampling area comprising an expandable tissue sampling element. A device of the present invention comprises an expandable tissue sampling element. A device of the present invention comprises a sampling area comprising an expandable tissue sampling element comprising a sheath having at least one slit comprising two opposing edges wherein the two opposing edges may be moved apart from each other to expand the diameter of sheath so that the diameter of the sheath is greater where the two opposing edges are moved apart from each other than the diameter of the sheath where there is no slit. An expandable tissue sampling element is expanded by the movement of the opposing edges of a slit away from each other and the tissue sampling element is reduced to its original state by the opposing edges of a slit moving together and being adjacent again. When the slit is open, so that the opposing edges of the slit are apart from one another, the sheath and/or sampling area is said to be expanded. When the slit is closed, so that the opposing edges of the slit are substantially adjacent to one another, the sheath and/or sampling area is not expanded.

Since it was first described in publication in 1943 by Dr. Papanicolaou, the Pap smear has been the gold standard in the screening for cervical cancer. As with any screening test it was designed to be highly sensitive but not very specific. The standard management of patients with an abnormal pap smear is colposcopic examination of the cervix, which may include directed cervical biopsies and may include an evaluation of the inside of the cervical canal by endocervical curettage (ECC). The criteria for an adequate colposcopy are complete visualization of the entire transformation zone and the squamocolumnar junction and clear definition of the extent of cervical lesion. One of the reasons for colposcopy failing to identify invasive carcinoma is the presence of cancer in the endocervical canal not visualized at the time of the colposcopic examination of the cervix. Most cervical cancer screening programs rely on cervical cytology followed by diagnosis of screening-detected abnormalities using colposcopic biopsy. ECC may be performed at the time of colposcopy with or without local anesthetic. ECC was recommended in the early 1980s as a way to reduce the risk of incorrectly treating women with invasive cancer by ablative therapy. Today ablative therapy is rarely used and the treatment of choice most often involves a loop electrical excision procedure (LEEP). In most cases, the threshold for excisional treatment of the cervix is histological CIN2 (cervical intraepithelial neoplasia grade 2) or greater. However, a diagnosis of CIN2 is poorly reproducible between pathologists and often includes both transient HPV infections and early pre-cancers. These cases may regress spontaneously, however, in most settings CIN2 is treated immediately resulting in frequent overtreatment that can lead to obstetric complications in the future. In addition, excision techniques are recommended for patients in whom the entire lesion cannot be visualized by colposcopy or the colposcopic examination is unsatisfactory as a colposcopic examination can miss the earliest and most treatable lesions, also amplifying the problem of overtreatment.

There has been much debate over the past several decades about the clinical utility of an ECC. The technique can be problematic in terms of discomfort to the patient, adequacy of specimen collection, pathologic interpretation with reported high false-positive and false-negative rates, and cost. However, not performing an ECC during a colposcopy has been considered by many, a diagnostic error as invasive cancer can be missed. The clinical need to detect colposcopically occult disease or decide the extent of excisional therapy based on ECC is confounded by the low diagnostic yield and potential contamination of ECC specimens, especially when lesions are located near the os. The value of the ECC remains controversial as the false-positive results are thought to be primarily due to contamination of the specimen from an ectocervical lesion as demonstrated by Moniak et al, which noted that ECC has a high positive predicative value (86%) for ectocervical disease. Although a false-positive ECC may result in overtreatment, a false-negative result may result in missing invasive disease. In addition to the false-positive and false-negative rates for an ECC, another major clinical disadvantage is the high rate of inadequate samples, which has been reported to be as high as 22%. In 1988, Andersen et al. published results that ECC misses nearly 50% of all endocervical lesions. Furthermore, sensitivity and specificity of the ECC device is critical in devising an acceptable device. Improvements to specificity have been made by encasing the collection end (i.e. brush) in a protective sleeve to avoid ectocervical contamination as noted by Gosewehr et al.

No screening test, however, has 100 percent sensitivity, and a wide range of false-negative rates for a single Pap smear have been reported. A fifteen to twenty-five percent false-negative rate for pap smears is widely accepted, as cervical cancer usually develops over long periods of time and repetitive screening usually can catch lesions to be treated. Sampling false-negatives (absence of abnormal cells on the smear) are slightly more common than laboratory false-negatives, which are divided about evenly between screening errors and interpretation errors. The presence of endocervical cells, which are characteristically glandular-type cells, are necessary for an adequate smear. Low-grade squamous (exocervical cells) intraepithelial lesions (LSIL) account for most false-negatives, and about half of these regress. For those that progress, evolution is usually slow, and thus the consequences of a false-negative are minimized by an annual Pap smear. Twenty to thirty percent of women with LSIL on Pap smear, however, will have high-grade squamous intraepithelial lesion (HSIL) on biopsy.

Lesions missed by Pap smear are summarized as follows: (1) those that occur outside of a large eversion (where the endocervical tissue tends to roll out from the cervical os and corresponds to the original squamocolumnar junction of newborns and young females), (2) small lesions, (3) advanced invasive lesions since they have infection and necrotic tissue, which can obscure the true cytology, (4) rapidly progressive lesions, and (5) lesions deep in the cervical canal. An optimal cervical specimen includes sampling of the squamous and columnar epithelium, encompassing in particular the transformation zone, where the majority of cervical neoplasias arise. Carcinogenic HPV (human papillomavirus) infections are particularly prone to cause cancer at transformation zones where two kinds of epithelium meet. Specifically the transformation zone of the cervix has squamous epithelium gradually undermining and being replaced by glandular epithelium (squamous metaplasia). The endocervical limit of the transformation zone is dynamic, defined by the leading edge of the migrating squamo-columnar junction. Squamous metaplasia continues throughout a woman's life and eventually the transformation zone is located inside the cervical os. Therefore in post menopausal women, it is often high in the endocervical canal and not visible. Clinicians are challenged to identify the transformation zone, which is of the utmost importance because cervical cancer and its precursors typically begin within this area; therefore, sampling in this area is critical in accurate screening and diagnosis.

A number of devices have been developed to collect samples from the cervix, including brushes, cotton swabs, spatulas, and applicators. Although, cytologic screening reduces mortality from cervical cancer by earlier diagnosis of invasive disease, there is still an unacceptable false negative rate due to the sampling brushes used and the method by which a sample is obtained. The most common instrument used to perform an ECC is called the Kevorkian, offered in metal or plastic that requires multiple entries into the patient's endocervical canal, using firm strokes from the lower uterine segment to the external cervical os, to obtain a representative sample of the entire area of interest. The Kevorkian devices' sampling areas are rectangular in shape and in order to contact the surface of the cervical canal, the physician must apply force during sampling, and essentially inserts a rectangle into a cylinder and forces the hard corners of the rectangles against a curved surface. An effort may be made to rotate the curette to ensure sampling of the entire 360° circumference but this is often difficult if not impossible to attempt due to patient pain/discomfort. Care is taken to avoid curettage of the lower uterine segment of the exocervix. In addition, efforts are usually made to collect the curetted sample within the endocervical canal and remove the currette's jaws without tearing off lesional tissue that could be located close to or at the external os. Fine tipped forceps, suction devices (i.e. pipettes), ectocervical biopsy instruments, or other techniques may be used to retrieve any additional material in the canal.

The current ECC devices, including the Kevorkian Curette obtain a questionable sample at the expense of subjecting the patient to a painful procedure. The current device designs lend themselves to a high and concerning false positive rate due to the contamination of the targeted endocervical sample with ectocervical tissue. This high false positive rate often leads to unnecessary and often destructive cervical surgical excisional procedures when the sample is analyzed by a laboratory and those patients with positive or questionable results are asked to return for a loop electrosurgical excision procedure (LEEP). In addition, the tissue sample quantity collected by the current device designs is often inadequate for pathological evaluation. This shortcoming of the current device designs often lead to a high false negative rate. Those with negative results are recommended to undergo repeat pap smear screening, ECC and colpscopy. Furthermore due to the current device designs it is unlikely that a complete sample of the endocervical canal will be obtained so detection of pre-cancerous or cancerous cells may be missed.

The currently used or available device designs have inherent deficiencies that affect their ability to be a reliable and useful tool in diagnosing advanced cervical lesions. The ideal ECC device is one that is simple, minimizes discomfort or pain for the patient and most importantly provides a comprehensive and adequate volume sample that is minimally contaminated of the endocervical canal. The overwhelming goal of the contemplated device designs are to address the shortcomings of the current device designs with an easy to use device applicable to a variety of anatomical cervical variants, to decrease the frequency of false negatives allowing for improved detection rates of early high grade lesions and reduce false positives to decrease the number of unnecessary surgical treatments.

The present invention comprises methods and devices useful for obtaining the intended tissue sample of a body conduit under controlled conditions, for example, where the tissue are located in the cervix. For example, the present invention comprises methods and devices for use in capturing a complete, adequate, and minimally contaminated sample with single or minimal number of entry insertions into the cervix. The devices can be designed to be reusable or disposable for single use.

A device of the present invention may be sterile, disposable endocervical sampling device with indications for single patient use in obtaining tissue samples from the endocervical canal for histological analysis. Clinical indications for performing a method of the present invention using a device disclosed herein include, but are not limited to, further evaluation of an abnormal Pap smear; further evaluation of two successive normal Pap smears accompanied by two successive positive high-risk HPV tests; unsatisfactory colposcopy; cervical lesions extending into the endocervical canal; as a diagnostic device in patients with high grade cervical lesions; in surveillance after surgical treatment of high-grade cervical lesions, for undiagnosed uterine bleeding, and as a substitute for a pap smear for women of advanced age or with other clinical sequelae. A device of the present invention may collect a targeted complete tissue sample with minimal ectocervical contamination that is adequate in volume for histological evaluation.

A device of the present invention comprises a sampling area comprising a sample collection cavity comprising a portion of a wand having a reduced diameter and an overlaying sheath having at least one slit that is capable of providing an opening within the sheath for access to the sample collection cavity beneath. The slit may have two opposing edges. There may be one or more slits in the sheath forming one or more access sites to the sample collection cavity. The slit may be in an open or closed position. In a closed position, the opposing edges of the slit are adjacent and adjoin each other so as to substantially close the slit and to prevent access to the sample collection cavity underlying the slit or slits. In an open position, the opposing edges of the slit are apart from each other to form an opening so that the sample collection cavity may be accessed. In an aspect, when the opposing edges are moved apart from each other, the diameter of the area of the sheath where the slit occurs is greater than the diameter of the area of the sheath where the slit occurs when the opposing edges are substantially adjoined or a closed position. The open position is also referred to herein as being expanded. When the opposing edges of a slit are moved apart from each other, each edge is exposed and forms a scraping edge, and the opposing edges form a tissue sampling element that is used to remove tissue from a soft tissue location. The removed tissue enters the sample collection cavity through the opening formed by the moved apart opposing edges. The removed tissue (a sample) is contained within the sample collection cavity and the opposing edges are moved together to substantially close the sample collection cavity so that no further tissue can enter the sample collection cavity to contaminate the sample and so that the sample does not leave the sample collection cavity and be lost.

Figure 2:
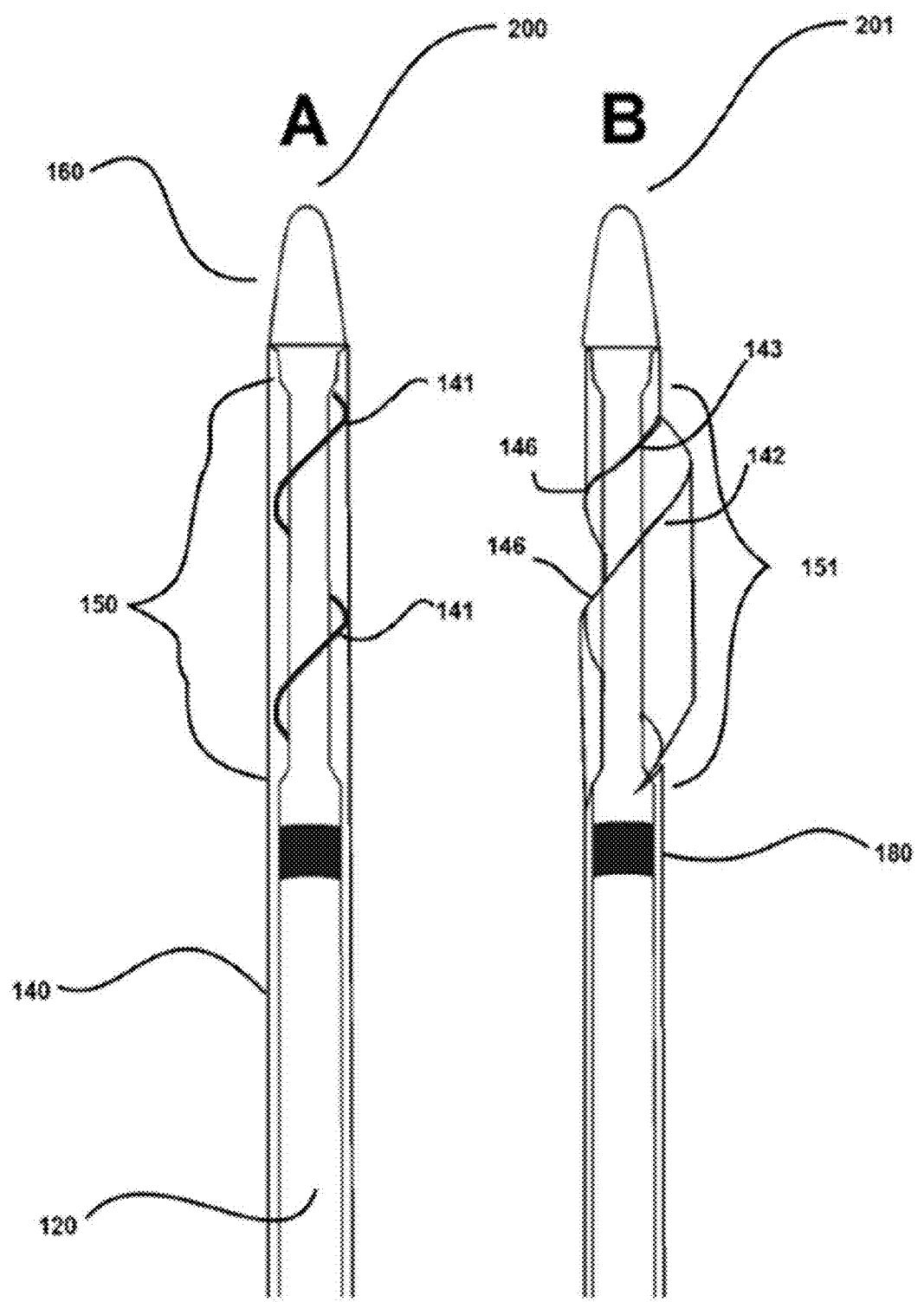
FIGS. 2A and B shows an enlarged view of a sampling area of the device of FIG. 1.
Figure 3:
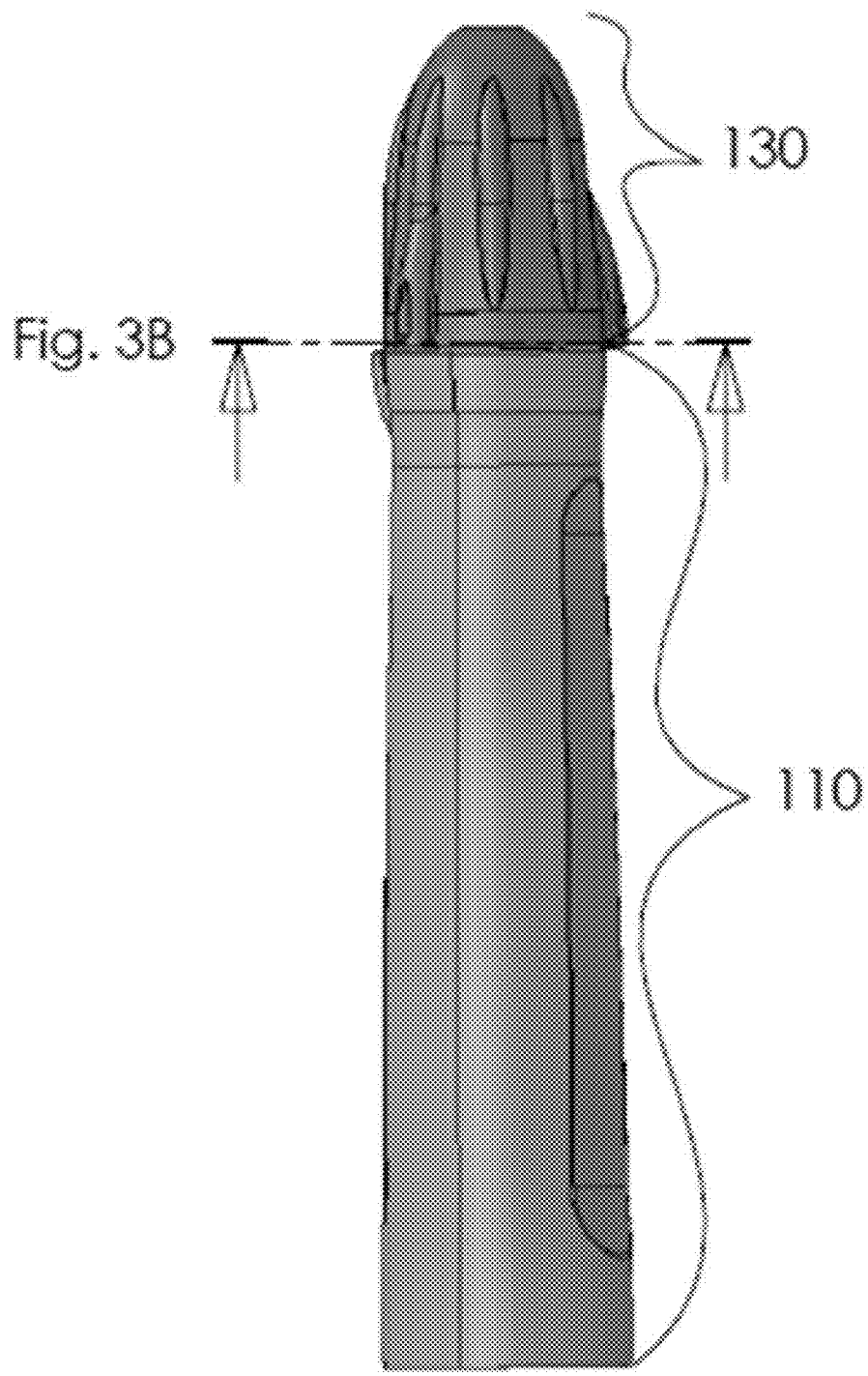
FIGS. 3A and B show an enlargement of the handle and actuator portions of the device of FIG. 1, wherein 3A is an exterior view and 3B is a cross-sectional interior view.
Figure 3:
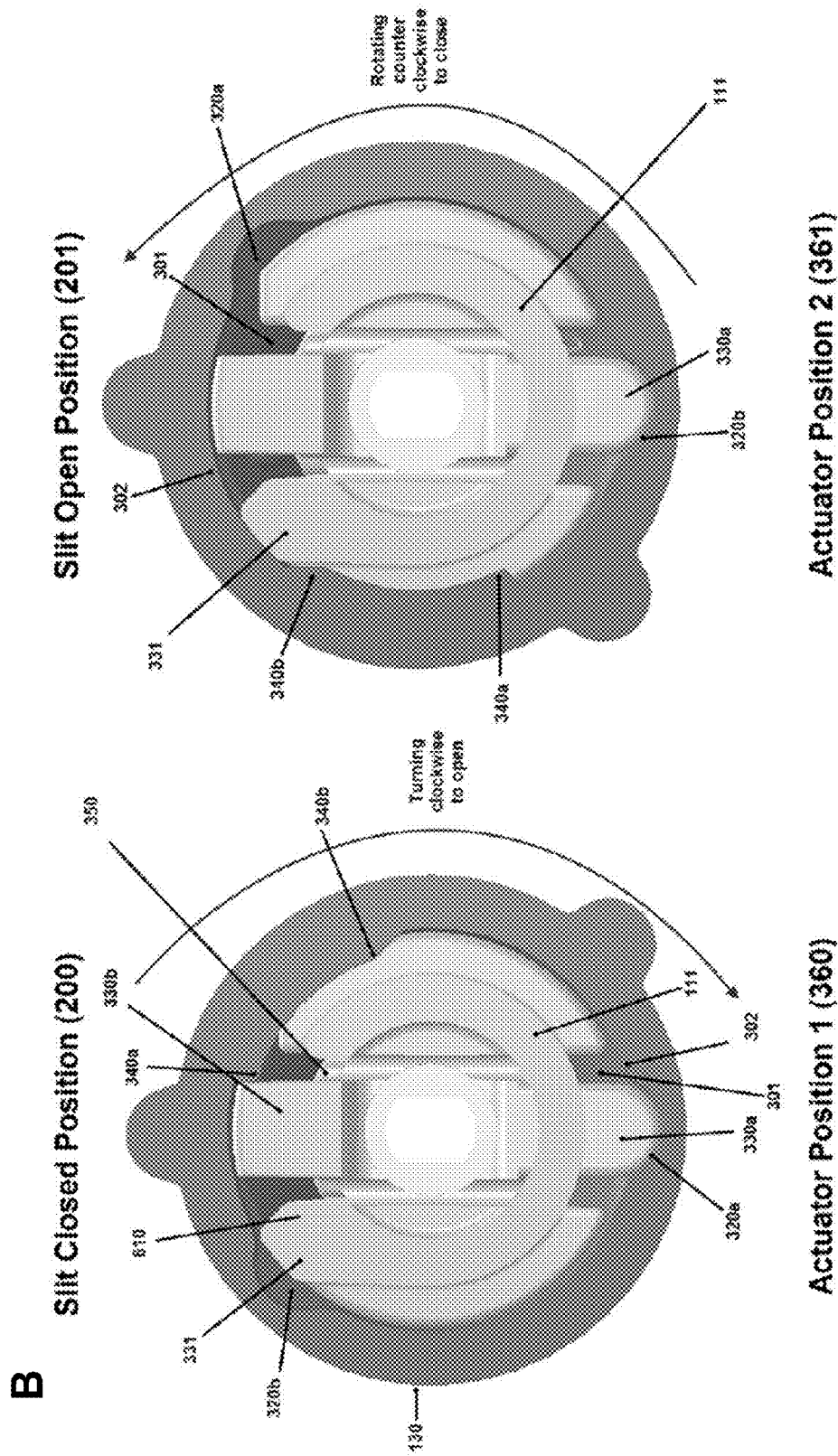
Figure 4:
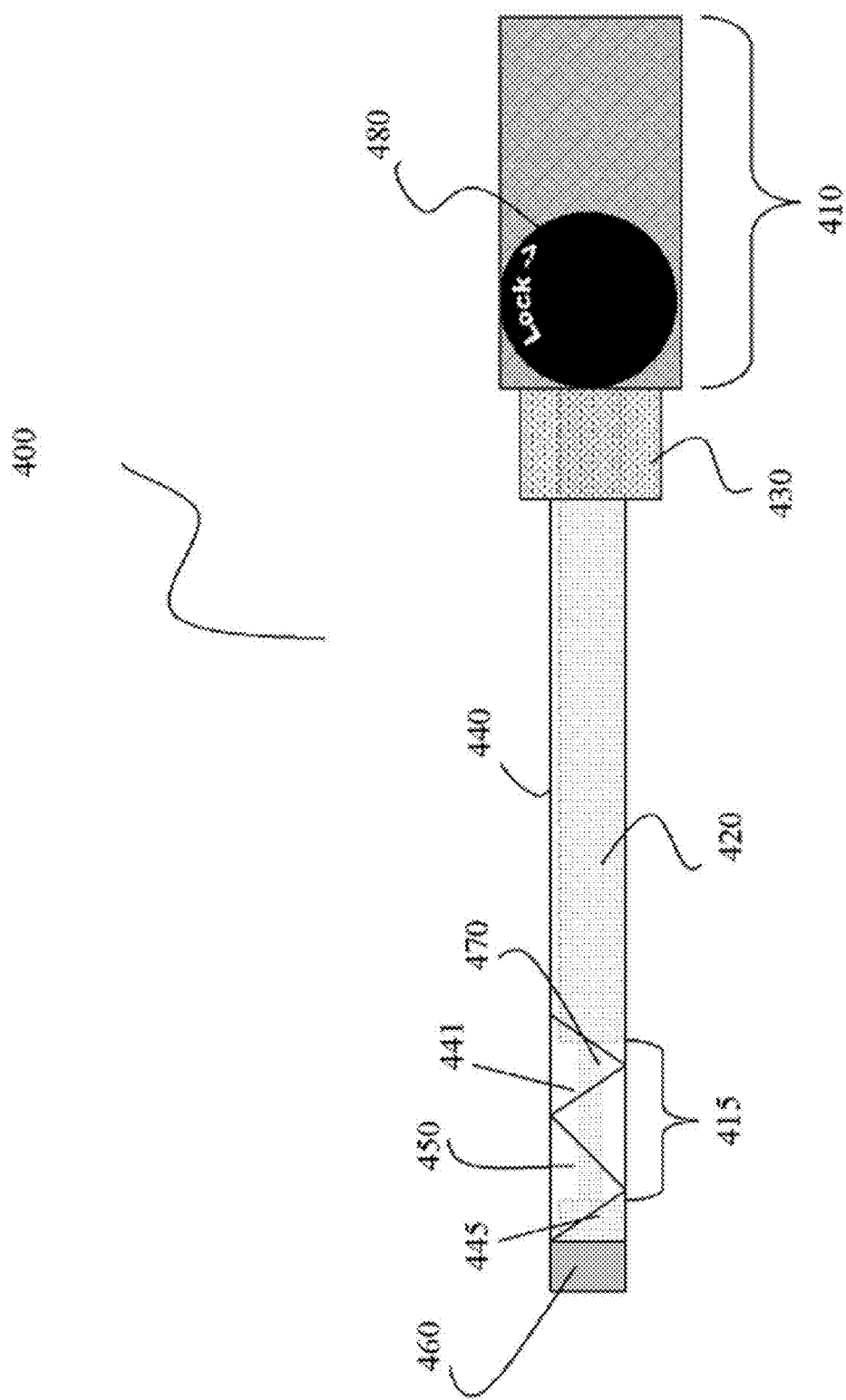
FIG. 4 shows an exemplary device of the present invention.
Figure 5:
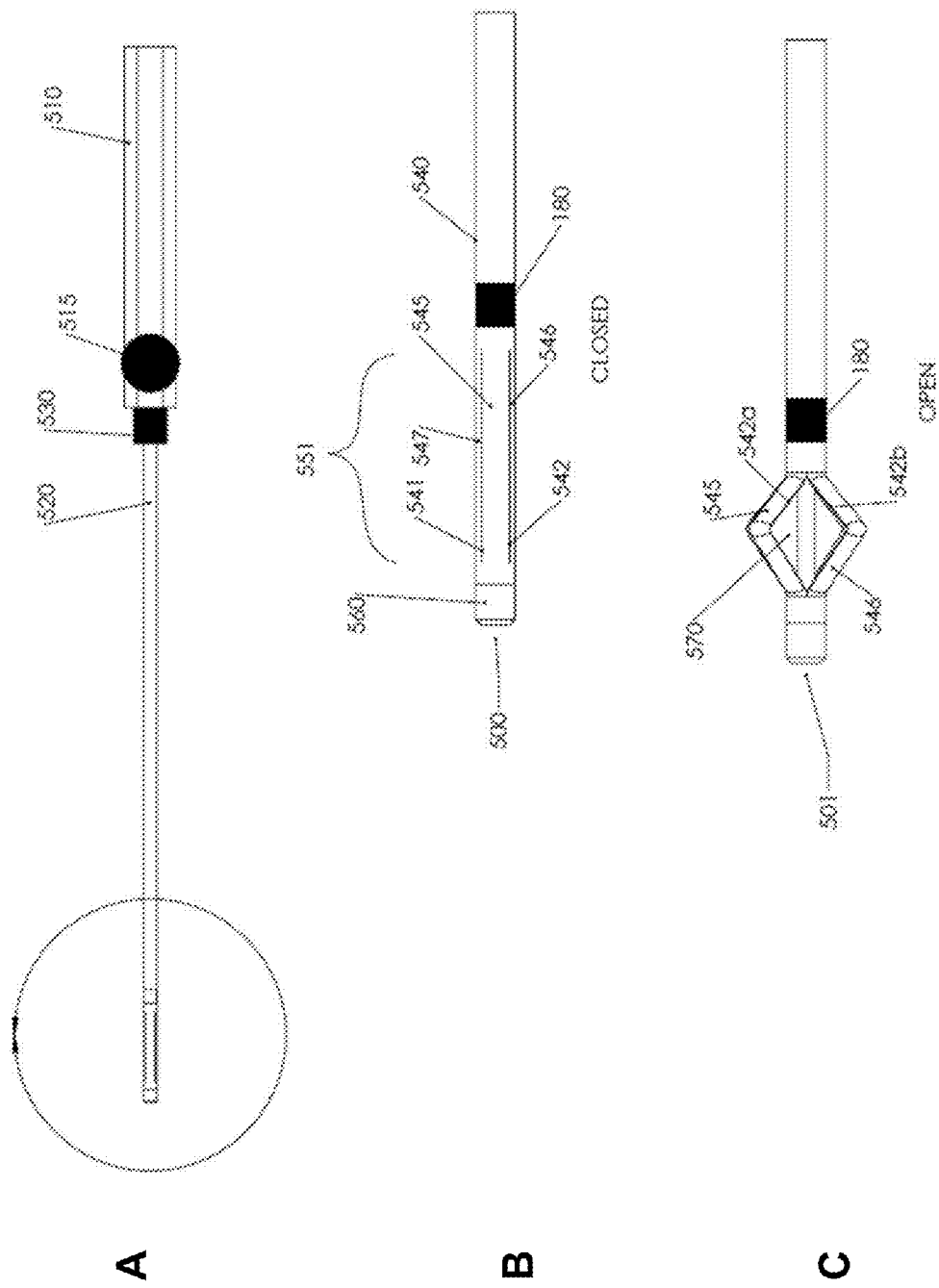
FIGS. 5 A-C show an exemplary device of the present invention, where 5B and 5C are enlargements of the distal portion of the exemplary device shown in 5A.
Figure 7:
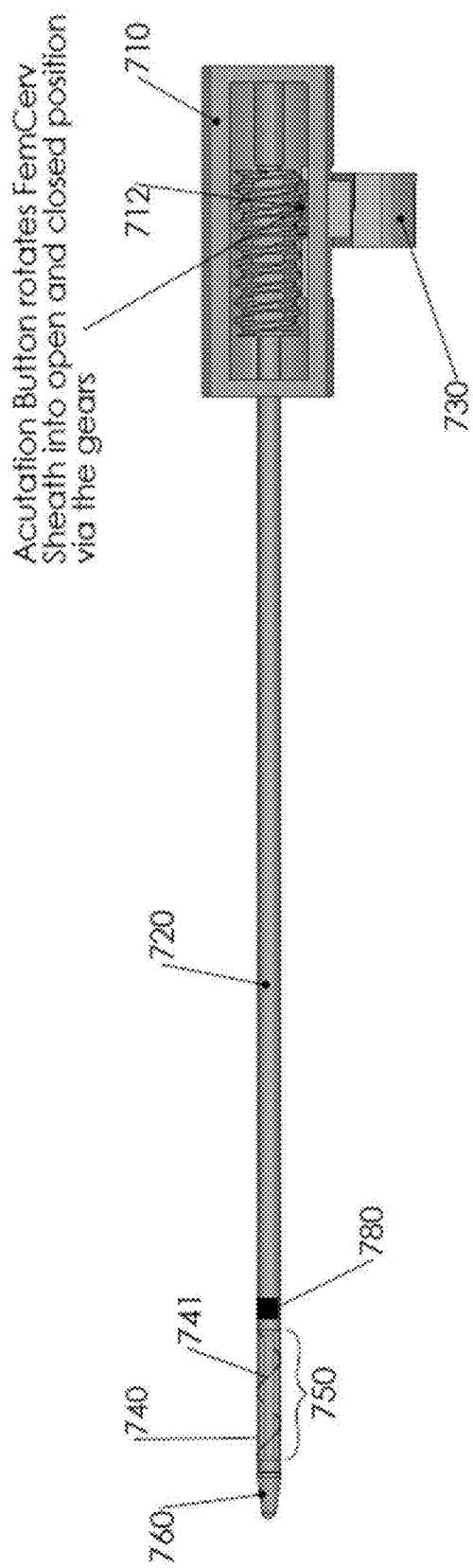
FIG. 7 is an exemplary example of a device of the present invention.

The present invention comprises a device for sampling the cervix, comprising endocervical and transition zone areas. An exemplary device is shown in FIGS. 1, 2, 3 A and B, and 6, and exemplary devices are shown in FIG. 4, FIG. 5 and FIG. 7, and described herein. Looking at FIG. 1, a device of the present invention comprises a cervical sampling apparatus 100, comprising, a handle 110 having a distal end 111 and a longitudinal axis, an elongated wand 120 extending outwardly from the distal end 111 of the handle 110 substantially along the longitudinal axis, wherein the wand 120 has an exterior surface, a front end 121 and a back end 122, and wherein the back end 122 is fixedly mounted to the distal end 111 of the handle 110; an actuator 130 rotatively coupled to the distal end 111 of the handle 110, the actuator 130 defining an opening at a first end 131 that is sized to rotatively receive a portion of the wand; a sheath 140 selectively encapsulating a portion of the wand 120 and fixedly mounted to a portion of the wand proximate to the front end 121 of the wand and to a portion of the first end 131 of the actuator 130, wherein the sheath 140 defines a slit 141 on a distal end portion of the sheath 140, the slit 141 being bordered by opposing edges 142 and 143, (see FIG. 2) wherein the distal end portion of the sheath 140 and a portion of the exterior surface of the wand underlying the distal end portion of the sheath define a sample collection cavity 150. As shown in FIG. 2, the slit 141 is selectively movable (expandable) between a closed position 200, (FIG. 2A) in which the opposing edges 142 and 143 of the slit 141 substantially adjoin to substantially seal the sample collection cavity 150, and an open position 201, (expanded) (FIG. 2B) in which the opposing edges 142 and 143 of the slit 141 are spaced from each other for obtaining a tissue sample when positioned within a cervix by contacting the surface of the endocervical canal. When spaced apart from each other, the opposing edges 142 and 143 form a tissue sampling element such that when contacting a soft tissue surface is capable of removing tissue from a soft tissue surface, such as the inner surface of the endocervical canal. As shown in 2B, the sampling area 151 comprises an open sample collection cavity 150 with opposing edges 142 and 143 forming the tissue sampling element 146. Optionally, spaced from the proximal end of the sample collection cavity 150 is an indicator 180, which may be used as a depth indicator to a user to indicate the length of the apparatus inserted into the patient and approximate location of the sample collection cavity 150. A depth stop, not shown, may be located on or proximate to the indicator 180. The device may comprise a closed tip 160, such as an atraumatic tip, as shown in FIGS. 1 and 2.

As shown in FIGS. 3A and B, actuator 130 is selectively rotatable about the distal end 111 of the handle 110 between a first position 360, in which the slit 141 is positioned in the closed position 200 (shown in FIG. 2A), and a second position 361, in which the slit 141 is positioned in the open position 201 (shown in FIG. 2B). The slit 141 may be a helical slit 141 that extends about the longitudinal axis. The helical slit may comprise a plurality of helical slits. A slit may have at least one round 170 around the longitudinal axis. (See FIG. 1) The opposing edges 142 and 143 of the slit 141 may be oriented substantially parallel to each other and substantially normal to an exterior surface of the sheath 140 when the slit 141 is in the closed position 200. At least a portion of one of the opposing edges 142 and 143 of the slit 141 is oriented at an acute angle to the longitudinal axis when the slit 141 is in the open position 201. The opposing edges 142 and 143 of the slit may be oriented substantially parallel to each other and are positioned at a face angle relative to an exterior surface of the sheath 140 when the slit 141 is in the closed position 200. At least a portion of one of the opposing edges 142 and 143 of the slit 141 may be oriented at an acute angle to the longitudinal axis when the slit 141 is in the open position 201. In an aspect, the face angle is not normal to the exterior surface of the sheath 140.

In an aspect, the front end of the wand 120 defines a tip 160. (See FIGS. 1 and 2). The tip 160, such as an atraumatic tip, may be tapered for ease of entry of a device into the cervical os. The tip 160 may be made from the same or a different material as the wand, and may be more flexible than the wand for patient comfort. The distal end portion of the sheath 140 is positioned proximate to the tip 160 of the wand 120.

In an aspect, a portion of the wand 120 has a reduced diameter. In an aspect, the portion of the wand 120 having a reduced diameter underlies the distal end portion of the sheath. In an aspect, the portion of the wand 120 having a reduced diameter underlies the distal end portion of the sheath where a slit 141 is located. In an aspect, the portion of the wand 120 having a reduced diameter and the distal end portion of the sheath 140 where a slit 141 is located define a sample collection cavity 150.

See FIG. 3A which shows the exterior surface of handle 110 and actuator 130. FIG. 3B shows the interior view of actuator 130 as seen by looking from the handle towards the actuator in a distal direction, as sectioned along the line shown in FIG. 3A. In an aspect, actuator 130 defines an interior cavity 301 having an interior peripheral edge 302 having a plurality of spaced indentations 320 (320a and b) defined thereon and one or more actuator protrusions 340 (e.g., 340a and 340b). An actuator protrusion 340, when interacting with the distal end 111 of handle 110, may prevent the actuator 130 from continuing to rotate in a particular direction, depending on the location of the actuator protrusion. For example, when actuator 130 is in Position 1 (360), protrusion 340a stops actuator 130 from rotating further in a counterclockwise direction. Similarly, when actuator 130 is in Position 2 (361), actuator protrusion 340b stops actuator 130 from rotating further in a clockwise direction.

Figure 6:
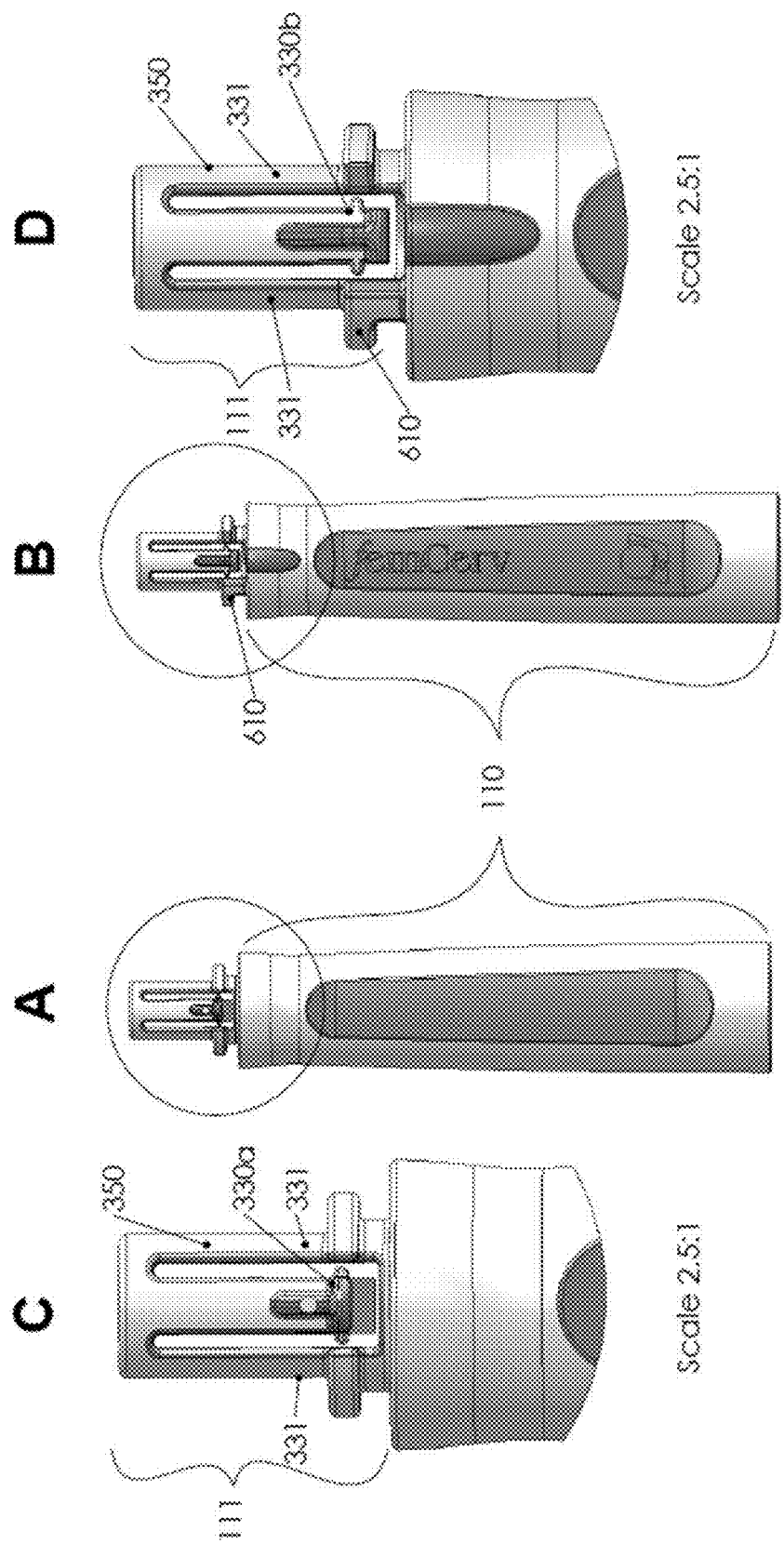
FIGS. 6A-D show the distal end of the handle of a device of FIGS. 1 and 3, wherein A is a front view, C is an enlargement of A, B is a back view and D is an enlargement of B.

Looking at FIGS. 3B and 6, the distal end 111 of the handle 110 defines a handle protrusion 350 extending distally along the longitudinal axis, the handle protrusion 350 defining a plurality of radially biasable keys 330 and a stationary portion 331. The radially biasable key 330a is configured to be selectively received therein the plurality of indentations 320 (e.g., 320a and 320b) in the respective first 360 and second 361 positions. A shown in FIGS. 3A and 6, key 330a is rounded so as to fit within a rounded indentation 320a and 320b. Key 330b acts as a radially biasable key during assembly of the device and then it acts as a non-biasable key during device operation since it does not interact with the spaced indentations 320 during actuation/rotation. Stationary portion 331 provides a stop 610 to impede the movement of actuator 130. In an aspect, the plurality of spaced indentations 320 comprise a pair of spaced indentations 320 positioned between about 110° to 140° apart. In an aspect, the plurality of radially biasable keys 330 (e.g., 330a and 330b) comprise a pair of spaced radially biasable keys 330 positioned between about 170° to 190° apart. In an aspect, the pair of spaced radially biasable keys 330 are positioned about 180° apart. In an aspect, moving the actuator position from closed 360 to open 361 requires a rotation between about 220° to 250°.

Optionally, the elongate wand 120 is flexible. Optionally the distal end of the device comprising the sampling area 151 is detachable. For example, (not shown) the distal ends of the sheath and shaft, comprising the sampling area 151, both could be scored so that with pressure or cutting, they break away from the rest of the device. A scored line around the diameter of the shaft could be used to create a weak section in the shaft so that the shaft would break when flexed. Depending on the sheath material, the sheath may or may not need to be scored also. In an aspect, the sampling area could be removed intact by cutting it off with a cutting tool or knife. Alternatively, the distal end of the device could be sheared off using, a cutting tool.

A device of the present invention comprises a cervical sampling apparatus 100 comprising, a handle 110 having a distal end 111 and a longitudinal axis; an elongate wand 120 extending outwardly from the distal end 111 of the handle 110 substantially along the longitudinal axis, wherein the wand 120 has an exterior surface, a front end 121 and a back end 122, and wherein the back end 122 is fixedly mounted to the distal end 111 of the handle 110; an actuator 130 rotatively coupled to the distal end 111 of the handle 110, the actuator 130 defining an opening at a first end 131 that is sized to rotatively receive a portion of the wand 120; a sheath 140 selectively encapsulating a portion of the wand 120 and fixedly mounted to a portion of the wand proximate the front end 121 of the wand 120 and to a portion of the first end 131 of the actuator 130, wherein the sheath 140 defines a slit 141 on a distal end portion of the sheath 120, the slit 141 being bordered by opposing edges 142 and 143, wherein the slit 141 is selectively movable between a closed position 200, in which the opposing edges 142 and 143 of the slit 141 substantially adjoin to substantially seal a sample collection cavity 150, and an open position 201, in which the opposing edges 142 and 143 of the slit 141 are spaced from each other for selectively obtaining a tissue sample when positioned within a cervix. In an aspect, the actuator 130 is selectively rotatable about the distal end 111 of the handle 110 between a first position 360, in which the slit 141 is positioned in the closed position 200, and a second position 361, in which the slit 141 is positioned in the open position 201. In an aspect not shown, the actuator 130 may selectively rotatable about the handle 110 between a first position 360, in which the slit 141 is positioned in the closed position 200, and a second position 361, in which the slit 141 is positioned in the open position 201, where the actuator 130 is located on the handle at a location proximal to the distal end, such as in the middle of handle 110 or at the proximal end of handle 110. In an aspect, the distal end portion of the sheath 140 and a portion of the exterior surface of the wand 120 underlying the distal end portion of the sheath define a sample collection cavity 150. Optionally, an indicator 180 is located proximally to sample collection cavity 150. In an aspect, the slit 141 is a helical slit that extends about the longitudinal axis. A slit 141 may have at least one round 170 around the longitudinal axis.

As shown in FIGS. 3B and 6, in an aspect, actuator 130 defines an interior cavity 301 having an interior peripheral edge 302 having a plurality of spaced indentations 320 defined thereon, wherein the distal end 111 of the handle 110 defines a handle protrusion 350 extending distally along the longitudinal axis, the handle protrusion 350 defining a plurality of radially biasable keys 330, of which 330a is configured to be selectively received therein the plurality of spaced indentations 320 in the respective first 360 and second 361 positions. In an aspect, the plurality of spaced indentations comprise a pair of spaced indentations 320 (e.g., 320a and 320b) positioned between about 110° to 140° apart. In an aspect, the plurality of radially biasable keys comprises a pair of spaced radially biasable keys 330 (e.g., 330a and 330b) positioned between about 170° to 190° apart. In an aspect, the pair of spaced radially biasable keys 330 are positioned about 180° apart. In an aspect, moving the actuator position from closed 360 to open 361 requires a rotation between about 220° to 250°.

As shown in FIG. 3B, actuator 130 is moved from position 1 (360) to position 2 (361) by rotating actuator 130 around the handle 110 in a clockwise direction. Biasable key 330a is present in indentation 320a in position 1, and when the actuator 130 is rotated in a clockwise direction to position 2 (361), biasable key 330a then resides in indentation 320b. In position 1, actuator protrusion 340a abutting key 330b prevents actuator 130 from rotating in a counter-clockwise direction. In position 2, actuator protrusion 340b abutting stop 610 formed in stationary portion 331 prevents actuator 130 from rotating in the clockwise direction. Handle protrusion 350 does not rotate, though keys formed therein may be biased radially, but the handle protrusion 350 remains in one location (other than biasable keys moving inward and returning to the starting position radially) and interacts with the actuator protrusions and indentations.

FIG. 4 shows an embodiment of the present invention comprising a cervical sampling apparatus 400 comprising a sample collection cavity 450 formed by a distal section of the wand 420 having a reduced diameter and the overlying sheath 470, and having a sample area 415 comprising an expandable tissue sampling elementformed by a slit 441 comprising two opposing edges (not shown), which when moved apart from each other form a tissue sampling element (not shown). The device comprises a wand 420 and an overlying sheath 440, a slit 441 in the distal portion of the sheath, a handle 410 and a tip 460. FIG. 4 shows the device in a closed position.

In a device of the present invention, a sheath may be moved, and a slit may be opened, in a variety of methods, and the present invention is not limited to only those exemplified herein. Moving a sheath to affect the opposing edges of one or more slits, so that the opposing edges move apart from each other, may be accomplished using an actuator, and comprises holding one portion of the sheath immobile while activating an actuator which moves another portion of the sheath so that the force(s) in the sheath from the immobile portion and the moved portion force the opposing edges of a slit apart. Relieving the force(s) by returning the actuator and the moved portion of the sheath to their original locations brings the opposing edges of the slit together again to form the closed position.

As shown in FIG. 4, the sheath is affixed on its distal end 445 to the distal end of the wand 420 and/or to the tip 460. The proximal end of the sheath is affixed to an actuator 430, for example, a sheath nut. The sheath nut 430 is rotatable, and when it rotates, it also moves the sheath 440. In the first position, with no movement by the sheath, the slit 441, is closed with its opposing edges substantially adjacent and adjoining each other. When the sheath nut 430 is rotated to a second position, the sheath 440 moves and the opposing edges of the slit 441 move apart from each other, exposing the edges and expanding the diameter of the sheath in the area of the slit, as described above. The sheath nut 430 may be held in the second position by a locking member 480, which may be a screw element that is turned to engage the proximal end of the actuator 430, sheath nut (not shown).

In an aspect, the locking member 480 may be a sliding element that may be moved in a longitudinal direction along the longitudinal axis of handle 410 to engage the proximal end of the actuator 430 so as to hold the actuator 430 in the second position. In an aspect, the actuator 430 (sheath nut of FIG. 4) may be held in position 1 by locking member 480 that is a spring-loaded element such that when the locking mechanism is activated by pushing on the surface, an engaging element is released and the actuator is moved by the force of the release of the spring in a longitudinal direction along the axis of the wand or is rotated circumferentially around the wand to position 2. The actuator may be returned to position 1 by manual manipulation and reengaging the engaging element. In an aspect, the actuator may be held in position 2, after manual movement of actuator from position 1 to position 2, by activating a spring-loaded locking member 480 that engages with the actuator in position 2. The actuator may be returned to position 1 by any method, for example, by manual manipulation.

Position 2 may be one or more locations that are distally or rotatably removed from position 1. Position 2 may a defined distal location a defined rotational site or may be any distally or rotatably removed location chosen by the operator of the device. When position 2 is a defined distal location, or a defined rotational site, the extent of the movement of the opposing edges away from each other is the same uniform extent of movement away from each other, and the opposing edges are moved apart to the same distance each time the actuator is moved to position 2. When position 2 is an optionally chosen distally or rotatably removed distance from position 1, undefined by any particular structural stopping element, the extent of the distance between the opposing edges of a slit is also an optional distance. Having an optionally distally or rotatably removed distance location for position 2 allows for the opposing edges to be moved apart in a continuous range, from the maximum distance apart to a position of almost closed, and all positions thereinbetween, allowing for rheostat-like control of the amount of expansion of the sheath in the area of the slit by the movement of the opposing edges away from one another. Once the actuator is in position 2, the position 2 location of the actuator may be maintained by engaging a locking member to hold the actuator stationary, and, for example, the tissue sampling element (open exposed opposing edges of the slit) is then used to obtain a sample that is contained within the sample collection cavity.

In an aspect, such as shown in FIG. 7, an actuator may rotate a gear or set of gears. One example of such a device, which may or may not place the sheath under strain, is to have the actuator rotate a gear or set of gears which would transfer the longitudinal motion of an actuator into a rotational motion via a toothed ring attached to the proximal end of the sheath. FIG. 7 shows cervical sampling device of the present invention comprising a handle 710 that is cut longitudinally to show the interior of handle 710 comprising a gear system 712 which comprises a gear that is moved by action of the actuator 730 to move the gears and affect the sheath 740 which is affixed to the gear system 712. Actuator movement moves the gears from position 1 where the slit 741 is closed and the sample collection cavity 750 is closed, to position 2 (not shown) which opens the slit exposing the opposing edges to form the tissue sampling element and opens the sample collection cavity. An indicator 780 may be in place on the sheath 440 or the wand 720. A tip 760, such as an atraumatic tip, may be on the distal end of the wand. The sheath 740 is affixed proximate to the tip 760. After a tissue sample is acquired and resident in the sample collection cavity, the actuator 730 is moved so that the gears return to position 1, the slit 741 closes so that the opposing edges are substantially adjacent to one another, the sample collection cavity 750 is closed.

In an aspect, (not shown) an actuator may be moved in a longitudinal direction, in a proximal to distal direction, to move a sheath so that the opposing edges of a slit are moved apart from each other. An actuator is moved from its most proximal site, position 1, where the slit is closed with its opposing edges substantially adjacent to each other, and the sheath is not under strain, to a second position, position 2 which is distally removed from position 1. When in position 2, the movement of the sheath moves the opposing edges of the slit apart so that the tissue sampling element is formed, as described herein. The actuator may be held in position 2 by a locking member, which may be a screw element, a sliding element or other such elements known to those skilled in the art that may interact with the actuator, the wand, the sheath, and/or the handle to maintain the actuator in position 2 and maintain the slit in an open configuration with its opposing edges apart from each other. Position 2 may be one or more locations that are removed from position 1. Position 2 may a defined distal location a defined rotational site or may be any distally removed location chosen by the operator of the device. When position 2 is a defined distal location, the extent of the movement of the opposing edges away from each other is the same uniform extent of movement away from each other, and the opposing edges are moved apart to the same distance each time the actuator is moved to position 2. When position 2 is an optionally chosen distally removed distance from position 1, undefined by any particular structural stopping element, the extent of the distance between the opposing edges of a slit is also an optional distance. Having an optionally distally removed distance location for position 2 allows for the opposing edges to be moved apart in a continuous range, from the maximum distance apart to a position of almost closed, and all positions thereinbetween, allowing for rheostat-like control of the amount of expansion of the sheath in the area of the slit by the movement of the opposing edges away from one another. Once the actuator is in position 2, the position 2 location of the actuator may be maintained by engaging a locking member to hold the actuator stationary, and, for example, the tissue sampling element (open exposed opposing edges of the slit) is then used to obtain a sample that is contained within the sample collection cavity.

The sheath may be made from a material that forms a tube covering, a sheath, having a thin wall that retains its shape. Suitable materials include but are not limited to, general classes of plastics, PTFE, PEEK, polycarbonate, nylon, polypropylene, FEP, LDPE, Topas, and other such plastics. The sheath material may also be constructed from surgical grade metals or alloys, such as stainless steel and Nitinol. The sheath material may also be fashioned from thermoset plastics such as epoxies. For example, qualities such as rigidity and transparency provide aspects desired in a sheath. Additionally, a sheath having a thin wall that is rigid allows for the formation of opposing edges of the slit that aid in scraping tissue during use. The wall of a sheath may be from about 0.100 inches to about 0.001 inches, from about 0.001 inches to about 0.050 inches, from about 0.001 inches to about 0.030 inches, from about 0.010 inches to about 0.100 inches, from about 0.010 inches to about 0.020 inches, from about 0.001 inches to about 0.010 inches, from about 0.001 inches to about 0.005 inches, from about 0.050 inches to about 0.100 inches, and widths thereinbetween.

The sample collection cavity is a contained space that cannot be accessed except when the slit is in an open position. Containing a sample within the closed sample collection cavity or having the cavity itself protected by being closed protects from contamination by the presence of other types of cells and prevents sample disruption or tissue loss, such as during insertion or removal of the cervical sampling apparatus into or from the patient.

A slit may comprise one or more revolutions or rounds around the longitudinal axis of the sheath. For example, one revolution to ten revolutions may be made in a sheath, with consideration of the rigidity of the material and ability of the edges of the slit to provide an adequate scraping to obtain a sample. The number of revolutions of the slit around the longitudinal axis may affect the number of rotations of the sample collection cavity and the choice of direction, whether in one direction or both clockwise and counterclockwise, used and may be determined by the sample to be collected. One skilled in the art can determine, without undue experimentation, if an adequate sample is collected by a device of the present invention having a slit with a particular number of revolutions, and rotation number and direction.

A slit may comprise one or more slits, each slit having opposing edges. In an aspect, such as shown in FIG. 5, four parallel slits are present in the distal end of a sheath of a device of the present invention, with two parallel slits shown, slit 541 and slit 542. The present invention contemplates devices having one or more slits. Such slits may be shaped as helical slits, longitudinal slits or perpendicular slits, or combinations of any of these. A longitudinal slit parallels the longitudinal axis of the wand. A perpendicular slit is a slit cut perpendicular to the longitudinal axis of the wand, and may comprise a slit that extends in a radial direction around a portion of the circumference of the sheath. Additional slit design comprises a plurality of slits, for example, with four slits parallel to the longitudinal axis of the wand, and a small slit connected to and perpendicular to each long slit. The small slit can be anywhere along the long slit, and the small slit may provide a different shape to the tissue sampling element, i.e. the small slit location can change the bend location of the exposed opposing edges when the sheath is moved to the open position.

An exemplary device is shown in FIG. 5 comprising a handle 510, a sheath 540, an actuator 530, a wand 520, and a locking member 515. When sheath 540 is moved in a longitudinal direction from a proximal position 1 to a distally removed position 2, the opposing edges of the parallel slits 541 and 542 are moved apart from each other, such movement also occurs with the other slits As shown in FIG. 5, slit 542 is bounded by area 545 and 546. When the opposing edges of slit 542 are moved apart, opposing edge 542a forms one border of area 545 and opposing edge 542b forms one border of area 546. The opposing edges 542a and 542b are capable of removing tissue when contacting a soft tissue surface, and form a tissue sampling element. Slit 541 is bounded by area 545 and area 547. When opposing edges of slit 541 are moved apart, opposing edge 541a forms one border of area 545 and opposing edge 541b forms one border of area 547 (not shown). The opposing edges 541a and 541b are capable of removing tissue when contacting a soft tissue surface, and form a tissue sampling element. The tissue sampling element formed by the movement of the opposing edges of the slits apart from each other may be used to collect a sample, and the sample is contained within the sample collection cavity formed by the reduced diameter of the wand and sheath overlying the area where the slits are located. Simultaneously, the slits 543 and 544 (not shown) are acted on to move apart so that each slit's opposing edges to form additional opposing edges for collecting a sample, tissue sampling elements.

In FIG. 5, a closed position 500 is shown and the actuator 530 is in position 1, with no movement forces on the sheath 540. The actuator 530 is moved to position 2 which moves the sheath so that the opposing edges of each slit are moved apart from each other, shown as the open position 501. The actuator 530 is moved from position 2 to position 1 to return the slits 541, 542, 543 and 544 to a closed position 500. The actuator may be held in position 1 or position 2 by a locking member 515. A tip 560 may be present. The sheath 540 may be affixed, as described for other exemplary devices, to both the wand and the actuator. An indicator and/or a depth stop may be located proximate to the sampling area comprising the sample collection cavity 570 and the slits 541, 542, 543 and 544.

In use of a device of the present invention, the distal end of the device is inserted into the cervical canal, optionally using the tip 560, such as an atraumatic tip, to dilate the cervical os to some extent, so that the sampling area comprising a sample collection cavity is positioned in the desired location in the endocervical canal. The distance of insertion of the device may be confirmed by an indicator 180 located on the sheath or wand, or by a depth stop, which is a physical stop for the operator. For example, a depth stop may be positioned, such as slidably moved into position, at the indicator location or in a substantially equal distance from the distal end of the wand. A depth stop may be affixed to a particular location on the wand and/or sheath and such location may be proximate to the proximal end of the sampling area.

Once the sampling area of the a device is in the desired location, the actuator is moved from position 1 to position 2 so as to move the sheath which causes the opposing edges of the slits present in the sheath to move apart from each other. The actuator may be maintained in position 2 by mechanisms and components described herein. The expansion of the sheath diameter at the slit(s) location allows for the opposing edges to contact the inner wall of the endocervical canal without the need to move the entire device. Exposing each of the opposing edges by their movement apart from each other forms the tissue sampling element of the device. The exposed opposing edges are moved in a direction, either longitudinally along the longitudinal axis of the device, such as distally and proximally from the original starting location, or circumferentially around the interior of the endocervical canal, or both, or multiple movements in both forward and reverse directions, and tissue from the soft tissue surface of the endocervical canal is removed and collected in the sample collection cavity. When sample collecting is complete, the actuator is moved from position 2 to position 1, and the opposing edges of the slits present in the sheath are moved together to adjoin so as to substantially close the sample collection cavity. The device is withdrawn from the patient. The sample is then removed from the sample collection cavity by moving the actuator from position 1 to position 2, thus opening the sample collection cavity by moving the opposing edges of the slit apart from each other, and the tissue contained within the sample collection cavity is removed by known methods. For example, the distal end of the device, comprising the sample collection cavity, may be placed in a container containing a histological fluid. The actuator is moved from position 1 to position 2 to move apart the opposing edges of the slit to expose the sample collection cavity and the tissue therein to be exposed to the histological fluid. The distal end of the device may be moved so as to wash the tissue from the sample collection cavity. The device may then be sterilized or discarded.

A slit may be cut into a sheath using any known cutting means, for example, by laser cutting. The cut made into the sheath for a slit may be perpendicular to the surface of the sheath and the longitudinal axis of the sheath, so that the opposing edges of the slit are oriented substantially parallel to each other and substantially normal to the exterior surface of the sheath when the slit if closed. The cut made into the sheath for a slit may be at a face angle to the surface of the sheath, so that the opposing edges of the slit are oriented substantially parallel to each other and positioned at a face angle relative to the exterior surface of the sheath when the slit if closed. When the slit is in an open position, at least a portion of one of the opposing edges of the slit are oriented at an acute angle to the longitudinal axis. Cutting a slit with edges at a face angle to the surface of the sheath may provide a slit having sharper cutting edges. Cutting a slit with edges that are saw toothed is also contemplated by the present invention. A slit having toothed opposing edges would provide a closed sample collection cavity by interleaving the teeth of each edge. The kerf or width of the cut to make the slit in the sheath should be minimized so that the sample collection cavity is adequately closed to prevent contamination or sample disruption. Cutting a slit removes material and the more material lost, as in making the kerf or width of the cut wider or larger, the less tightly the sample collection cavity will close.

The wand of the cervical sampling apparatus may be made from any material that provides rigidity and flexibility. Suitable materials include, but are not limited to, plastics, nylon, PEEK, stainless steel, surgical steels, Ultem, Torlon, PPS, Grivory, carbon fiber, graphite, and glass-filled Delrin, metals, any thermoplastic or thermoset material, including compositions that incorporate fillers or fibers to enhance sufficient rigidity. Considerations in choosing a material for a wand of a device of the present invention include high flexural modulus and sufficiently high rigidity, especially for the reduced diameter section of the wand. The reduced diameter section of the wand may have a diameter from about 0.100 inches to about 0.001 inches, from about 0.001 inches to about 0.050 inches, from about 0.020 inches to about 0.070 inches, from about 0.010 inches to about 0.100 inches, from about 0.010 inches to about 0.060 inches, from about 0.001 inches to about 0.080 inches, from about 0.050 inches to about 0.80 inches, from about 0.050 inches to about 0.100 inches, and widths inbetween. For example, the flexural modulus of Grivory is 2,680,000 psi, for unfilled polycarbonate is 375,000 psi, and 600,000 psi for unfilled PEEK.

A device of the present invention may have a wand of a particular diameter of the portion of the wand that does not form the sample collection cavity, which has a reduced diameter. The diameter may range from 0.050 inches to 1.0 inches, from about 0.100 inches to about 0.200, from about 0.120 inches to about 0.300 inches, from about 0.130 inches to about 0.200 inches, from about 0.140 inches to about 0.200 inches, from about 0.160 inches to about 0.200 inches, from about 0.100 inches to about 0.500 inches, from about 0.100 inches to about 0.700 inches, from about 0.050 inches to about 0.200 inches, and all diameters therein between. The length of a device of the present invention may be any desired length from the tip of the atraumatic tip to the proximal end of the handle. For example, the device may be from about 5 inches to about 25 inches, or from about 7 inches to about 15 inches, or from about 12 inches to about 15 inches, or from about 12 inches to about 20 inches, from about 5 inches to about 15 inches, and all lengths therein between.

The length of the insertion depth into the endocervical canal, as measured from the external cervical os, may be any desired and functional length, for example from 1 to 4 cm. The length of the area formed by the slit for total scraping length may be any desired length that provides an adequate and complete sample of the target area, and may be, for example, from about 0.3 inches to about 2.0 inches, from about 0.7 inches to about 1.2 inches, An indicator can be a marker band present on the distal end of the cervical sampling apparatus and may be on the wand, the sheath or both or a separate depth stop set to the uterine length. Such an indicator could be a marker band added to the wand or sheath by any means known, such as by pad printing on the wand or laser etching directly on the sheath. Alternatively, a material in a contrasting color to the wand or sheath may be applied to the wand or sheath, such as by heating the contrasting colored material to the surface or to an indentation in the surface of the wand, the sheath or both. The indicator may be of any width, such as from 0.05 inches to about 1.0 inches, that is of sufficient length to be viewed during use. The indicator is placed at a predetermined distance from the proximal end of the slit, and such distance may be from about 0.05 to about 0.5 inches from that end or set by the user once uterine length is determined. In use, the cervical sampling apparatus is placed into the patient to a depth where the indicator is just within the patient and no longer visible to the user or to a slideable depth stop set by the user, or an affixed depth stop is contacting the subject.

The sample collection cavity may have any volume desired that can be achieved by the volume of the space created by a reduced diameter wand portion and the overlaying sheath. As the diameter of a cervical sampling apparatus may be variable, for example to accommodate differing diameters of the endocervical canal, the diameter of a opened sheath, as measured at the extent of the opposed edges in an open position, may range from 0.05 inches to 1.0 inches, or from about 0.01 inches to about 0.75 inches, or from about 0.2 inches to about 0.5 inches, or from about 0.1 inches to about 0.3 inches, from about 0.05 inches to about 0.25 inches, and all diameters therein between. The sample collection cavity volume may differ also, and may range from 0.02 mL to about 1.2 mL. For example, the approximate volume of a sample collection cavity in a 9 FR device is 0.06 mL, the approximate volume of a sample collection cavity in a 11Fr device is 0.12 mL and the approximate volume of a sample collection cavity in a 13 Fr Device is 0.19 mL. A diameter of an opened sheath, as measured at the extent of the opposed edges in an open position, may be 0.223 inches. A diameter of an opened sheath, as measured at the extent of the opposed edges in an open position, may be 0.249 inches. A diameter of an opened sheath, as measured at the extent of the opposed edges in an open position, may be 0.288 inches.

In an aspect, the slit may be two separate slits, each of which is substantially parallel to the longitudinal axis of the device, and each is comprised of two opposing edges. When the actuator is moved from a first position to a second position, the opposing edges are separated from each other to provide an edge to be used for scraping and to open the sample collection cavity. The device functions in the manner and for the uses described herein.

A method of the present invention comprises using a device disclosed herein, such as one exemplified in FIGS. 1, 2, 3 A and 3B, and in FIGS. 4, 5, and 7 to obtain a sample comprising tissue and cells. As used herein, a sample may comprise tissue and cells, including intracellular matrix, and cellular and extracellular matter found when scraping or cutting an area of a human or animal, and may be referred to as tissue, cells or both.

A method of the present invention comprises obtaining a tissue sample, comprising providing a sampling device comprising a selectably movable sheath having at least one slit comprising opposing edges, wherein moving the sheath moves apart the opposing edges of the slit; placing the slit adjacent to a soft tissue site, moving the sheath so as to move the opposing edges of the slit apart from one another, collecting a sample by contacting the soft tissue with the opposing edges; moving the sheath so as to move the opposing edges of the slit adjacent to each other and substantially adjoining the edges; and removing the slit from the soft tissue site. The movable sheath overlays a portion of a wand. The selectably movable sheath comprises one or more slits, may comprise two slits, may comprise three slits, may comprise four slits, may comprise five slits, may comprise six slits, may comprise seven slits, may comprise ten or more slits. Moving an actuator affixed to the sheath moves the sheath. A device may comprise a wand, a moveable sheath, an actuator and a sample collection cavity. The sheath may be affixed to a distal portion of a wand (proximate to a front end) or a tip positioned on a distal end of the wand, and the sheath may be affixed to an actuator, or a component that is moved by an actuator.

A method of the present invention comprises a method of obtaining cervical samples, comprising, providing a cervical sampling apparatus 100, as shown in FIGS. 1, 2A and B, 3A and B, and 6. The method comprises providing a cervical sample apparatus comprising, a handle 110 having a distal end 111 and a longitudinal axis; an elongate wand 120 extending outwardly from the distal end 111 of the handle 110 substantially along the longitudinal axis, wherein the wand 120 has an exterior surface, a front end 121 and a back end 122, and wherein the back end 122 is fixedly mounted to the distal end 111 of the handle 110; an actuator 130 rotatively coupled to the distal end 111 of the handle 110, the actuator 130 defining an opening at a first end 131 that is sized to rotatively receive a portion of the wand 120; a sheath 140 selectively encapsulating a portion of the wand 120 and fixedly mounted to a portion of the wand proximate the front end of the wand and to a portion of the first end of the actuator, wherein the distal end portion of the sheath and a portion of the exterior surface of the wand underlying the distal end portion of the sheath define a sample collection cavity 150, wherein the sheath 140 defines a helical slit 141 on a distal end portion of the sheath, the helical slit 141 being bordered by opposing edges 142 and 143, wherein the helical slit 141 is selectively movable between a closed position 200, in which the opposing edges 142 and 143 of the helical slit substantially adjoin to substantially seal the sample collection cavity 150, and an open position 201, in which the opposing edges of the helical slit are spaced from each other; and wherein the actuator 130 is selectively rotatable about the distal end 111 of the handle 110 between a first position 360, in which the helical slit 141 is positioned in the closed position 200, and a second position 361, in which the helical slit 141 is positioned in the open position 201; introducing and advancing the distal end portion of the sheath to a desired location through the vaginal cavity into the cervical canal; rotating the actuator to the second position 361 to selectively extend the helical slit 141 to the open position 200; selectively urging the distal end portion of the sheath having opposing edges, wherein the opposing edges are urged against tissue at the desired location in the cervical canal while simultaneously rotating the handle 110 of the cervical sampling apparatus 100 to affect corresponding rotation of the open positioned helical slit to collect tissue into the sample collection cavity 150.

In an aspect, once the slit is positioned at a soft tissue site, to collect a sample, a cervical sampling apparatus with the slit in the open position may be rotated 360 degrees one or more times in one direction, such as clockwise. In an aspect, to collect a sample, a cervical sampling apparatus with the slit in the open position may be rotated 360 degrees one or more times in one direction, such as clockwise, followed by rotating the cervical sampling apparatus with the slit in the open position 360 degrees one or more times in the other direction, such as counterclockwise. In an aspect, to collect a sample, a cervical sampling apparatus with the slit in the open position may be rotated 360 degrees one time in one direction, such as clockwise, followed by rotating the cervical sampling apparatus with the slit in the open position 360 degrees one time in the other direction, such as counterclockwise. The number of rotations made in any one direction, and the direction of rotation, in one or both directions, may be variable, depending on the user and the sample desired. A method may comprise a step of collecting a sample, comprising rotating the handle of a cervical sampling apparatus which includes rotating the handle at least one, two, three, four, five, six, seven, eight, nine, ten or more complete revolutions, while the slit is in the open position, in one or both clockwise and counterclockwise. A benefit of the present invention is the ability to take a sample from the entire surface contacted by the device in an open position in a 360 degree rotation of the sample collection cavity. In an aspect, a portion of the handle, and not the entire handle, may be rotated so as to rotate and urge the tissue sampling element against the tissue surface. For example, a knob portion of the handle, in a distal or proximal portion of the handle, could be rotated so as to move the wand, sheath and sampling area comprising the tissue sampling element of the device along and/or against the tissue surface to collect cells and tissue.

In an aspect, in a method of collecting a sample, once the slit is positioned at a soft tissue site, to collect a sample, a cervical sampling apparatus with the slit in the open position may be moved in a longitudinal direction along the longitudinal axis of a cervical sampling apparatus, from a proximal location to a distal location along one or more longitudinal lines, one or more times. A method of collecting a sample may comprise moving the slit, which is in the open position wherein the opposing edges of the slit are moved apart from each other, by moving the cervical sampling apparatus in a longitudinal direction and in a circumferential direction, or one or both directions one or more times. Further the movement of the apparatus may be made so that a movement in a longitudinal direction comprises moving from site A in a distal direction to site B and returning from site B to site A by moving in a proximal direction. Further, the movement of the apparatus may be made so that a movement in a circumferential direction comprises moving from site A in a clockwise direction to site B or in a complete 360 degree rotation to site A again, and moving from site A in a counterclockwise direction to site B or in a complete 360 degree rotation to site A again. In an aspect, a method further comprises rotating the actuator to the first position 360 to selectively move the helical slit 141 to the closed position 200 to selectively close the sample collection cavity 150; and withdrawing the cervical sampling apparatus 100 from the vaginal cavity. In an aspect, the method may comprise selecting a cervical sampling apparatus having a wand plus sheath diameter that is appropriately sized for the patient on whom the apparatus is to be used. For example, for cervical anatomy having a small diameter, a cervical sampling apparatus having a diameter of from about 0.0.03 inches to about 3 inches may be used, and for cervical anatomy having a larger diameter, a cervical sampling apparatus having a diameter of from about from about 0.05 inches to about 5 inches or from about 0.1 inches to about 6 inches may be used. Apparatuses of the present invention may be provided in a range of wand plus sheath diameters, wherein the diameter is measured at an area where a slit is not located, of from about 0.03 inches to about 6 inches, and all diameters thereinbetween. For example, a wand plus sheath diameter, wherein the diameter is measured at an area where a slit is not located, is approximately 0.118 inches. For example, a wand plus sheath diameter, wherein the diameter is measured at an area where a slit is not located, is approximately 0.145 inches. For example, a wand plus sheath diameter, wherein the diameter is measured at an area where a slit is not located, is approximately 0.170 inches. For example, a wand plus sheath diameter, wherein the diameter is measured at an area where a slit is not located, is approximately 0.200 inches.

A method of the present invention comprises use of a device as shown in FIG. 4. A method comprises inserting into the endocervical canal of a female subject a device comprising a handle 410 having a longitudinal axis, an actuator 430 in a first position, a flexible wand 420, a sheath overlying the flexible wand 440, wherein the sheath comprises at least one slit 441 and is affixed proximate to the distal end of the wand and is affixed to the actuator, and a sampling area comprising the at least one slit and a sample collection cavity wherein the device is inserted to the extent that the sampling area 415 is within the endocervical canal; moving the actuator from a first position to a second position so as to move the opposing edges of the slit away from one another to form a tissue sampling element; optionally maintaining the actuator in a second position by moving a locking member; contacting the inner surface of the endocervical canal with the tissue sampling element by moving the entire device in a circumferential direction or in a longitudinal direction along the longitudinal axis of the device, or both to obtain a sample; containing the sample in the sample collection cavity; moving the actuator to the first position so as to move the opposing edges of the slit substantially adjacent to each other, and removing the device from the subject. The device may further comprise a tip 460, which may be an atraumatic tip or a closed tip.

An actuator 430 may comprise a sheath nut. Moving the actuator comprises rotating the sheath nut. Moving the actuator also moves the sheath 420. In a first position, with no movement by the sheath, the slit 441, is closed with its opposing edges substantially adjacent and adjoining each other. When the sheath nut 430 is rotated to a second position, the sheath 420 moves and the opposing edges of the slit 441 move apart from each other, exposing the edges, the tissue sampling element. The sheath nut 430 may be held in the second position by a locking member 480, which may be a screw element that is turned to engage the proximal end of the actuator 430 (not shown).

In an aspect, the locking member 480 may be a sliding element that may be moved in a longitudinal direction along the longitudinal axis of handle 410 to engage the proximal end of the actuator so as to hold the actuator in the second position. In an aspect, the actuator (sheath nut 430) may be held in a first position by locking member 480 that is a spring-loaded element such that when the locking mechanism is activated by pushing on the surface, an engaging element is released and the actuator is moved by the force of the release of the spring in a longitudinal direction along the axis of the wand or is rotated circumferentially around the wand to position 2. The actuator may be returned to position 1 by manual manipulation and reengaging the engaging element. In an aspect, the actuator may be held in position 2, after manual movement of actuator from position 1 to position 2, by activating a spring-loaded locking mechanism 480 that engages with the actuator in position 2. The actuator may be returned to position 1 by any method, for example, by manual manipulation. Position 2 may be one or more locations that are distally removed from position 1. Position 2 may a defined distal location or may be any distally removed location chosen by the operator of the device. When position 2 is a defined distal location, the extent of the movement of the opposing edges away from each other is the same extent, and the opposing edges are moved apart to the same distance. When position 2 is an optionally chosen distally removed distance from position 1, undefined by any particular structural stopping element, the extent of the distance between the opposing edges of slit 441 is also an optional distance. Having an optionally distally removed distance location for position 2 allows for the opposing edges to be moved apart in a continuous range, from the maximum distance apart to a position of almost closed, allowing for control of the amount of expansion of the sheath in the area of the slit 441. Once the actuator is in position 2, the position 2 location of the actuator is maintained by engaging a locking member to hold the actuator stationary, and, for example, the tissue sampling element is then used to obtain a sample that is contained within the sample collection cavity.

A method of the present invention comprises an actuator that moves a gear or set of gears, such as shown in FIG. 7. A method comprises providing to a female subject a device comprising an actuator in mechanical connection with a gear or set of gears that when activated, the gear or set of gears move a sheath such that opposing edges in one or more slits cut within the sheath are moved apart or away from each other. The device may further comprise a handle 710 comprising a gear system 712 which comprises a gear that is moved by mechanical action of the actuator to move the gears and affect the sheath 740 which is affixed to the gear system 712. Actuator movement moves the gears from a first position where the slit 741 is closed and the sample collection cavity 750 is closed, to position 2 (not shown) which opens the slit exposing the opposing edges to form the tissue sampling element and opens the sample collection cavity. An indicator 780 may be in place on the sheath 440 or the wand 720. An atraumatic tip 760 may be on the distal end of the wand. The sheath 740 is affixed proximate to the tip 760. After a tissue sample is acquired and resident in the sample collection cavity, the actuator is moved so that the gears return to position 1, the slit closes so that the opposing edges are substantially adjacent to one another, the sample collection cavity is closed. As used herein, the terms "a first position" and "position 1" may be used interchangeably, and similarly, the terms "a second position" and "position 2" may be used interchangeably and refer to the position of an actuator and/or the position of the opposing edges of a slit, as can be determined from a careful reading of the disclosure.

In a method, a device may be provided to a female subject comprising an actuator that moves in a longitudinal direction, in a proximal to distal direction, to move the sheath 420 so that the opposing edges of slit 441 are moved apart from each other. An actuator is moved from its most proximal site, position 1, where the slit is closed with its opposing edges substantially adjacent to each other, and the sheath 420 is not under strain, to a second position, position 2 which is distally removed from position 1. When in position 2, the movement of sheath 420 moves the opposing edges of the slit 441 apart so that the tissue sampling element is formed, as described herein. The actuator may be held in position 2 by a locking member 480, which may be a screw element, a sliding element or other such elements known to those skilled in the art that may interact with the actuator, the wand, the sheath, and/or the handle 410 to maintain the actuator in position 2 and maintain the slit in an open configuration with its opposing edges apart from each other. Position 2 may be one or more locations that are distally removed from position 1. Position 2 may a defined distal location or may be any distally removed location chosen by the operator of the device. When position 2 is a defined distal location, the extent of the movement of the opposing edges away from each other is the same extent, and the opposing edges are moved apart to the same distance. When position 2 is an optionally chosen distally removed distance from position 1, undefined by any particular structural stopping element, the extent of the distance between the opposing edges of slit 441 is also an optional distance. Having an optionally distally removed distance location for position 2 allows for the opposing edges to be moved apart in a continuous range, from the maximum distance apart to a position of almost closed, allowing for control of the amount of expansion of the sheath in the area of the slit 441. Once the actuator is in position 2, the position 2 location of the actuator is maintained by engaging a locking member to hold the actuator stationary, and, for example, the tissue sampling element is then used to obtain a sample that is contained within the sample collection cavity.

A method of the present invention comprises providing a device of the present invention to obtain a sample of endocervical tissue and/or cells that is representative of the types and numbers of cells in a particular location and is obtained by a complete transit of a circumferential area of the endocervix. In an aspect, a sample comprises a representative cellular sample of a particular area of the endocervix that can be reliably obtained. Reliably obtained means that the procedure can be accurately repeated and that a representative sample of substantially that same area can be obtained one or more times, such as to follow a course of treatment. A complete transit of a circumferential area of the endocervix means that in a particular location of the endocervix, such as a predetermined distance from the cervical os, a device of the present invention can reliably and reproducibly remove cells so that a representative sample of the cells in that area is obtained. A representative sample means a sample that has cells from the tissue surfaces in the area and the cells obtained represent the types and numbers of cells found in a 360 degree circumferential band around the interior surfaces of the endocervix, so that the cellular constituents present are sampled. A sample that is not a representative sample may provide inaccurate numbers or types of cells which may lead to unnecessary treatments or wrong diagnoses. A method for providing a complete and representative sample comprises providing the sampling area of a device of the present invention at the site of predetermined distance from the cervical os, contacting the inner surface of the endocervix by opening the one or more slits to form the tissue sampling element from the opposing edges of the slit, rotating the device at least one 360 degree rotation so that the tissue sampling element contacts the circumferential area of the endocervix at that location and removes at least cells from that area; retaining the removed cells in a sample collection cavity; and removing the device from the subject. The method may comprise more than one rotation and the rotations may be in the same or in the opposite direction, or may comprise rotations in the same and opposite directions. The method further comprises removing the sample from the device. The method further comprises examining the sample, for example, to make a diagnosis of the condition of the endocervix of the subject. A device of the present invention comprises a handle, a wand, and a sheath, wherein the wand and sheath form a sample collection cavity, wherein the sheath comprises at least one slit; and wherein the slit comprises at least two opposing edges that when moved apart from each other form a tissue sampling element. The device may comprise an actuator for moving the sheath which moves the at least two opposing edges of a slit apart from each other to form a tissue sampling element. The method further comprises, after obtaining the sample which is retained in the sample collection cavity, closing the slit so that the sample collection cavity is closed and the sample cannot be lost or cannot be contaminated during transit of the device into or out of the subject being sampled.

A method of the present invention comprises providing a device of the present invention to obtain a sample of endocervical tissue and/or cells that is representative of the types and numbers of cells in a particular location and is obtained by a complete transit of a longitudinal area of the endocervix. In an aspect, a sample comprises a representative cellular sample of a particular area of the endocervix that can be reliably obtained. Reliably obtained means that the procedure can be accurately repeated and that a representative sample of substantially that same area can be obtained one or more times, such as to follow a course of treatment. A complete transit of a longitudinal area of the endocervix means that in a particular location of the endocervix, such as a predetermined distance from the cervical os, a device of the present invention can reliably and reproducibly remove cells so that a representative sample of the cells in that area is obtained. A longitudinal area of the endocervix is defined by a path that runs from a site proximal to the cervical os to a site more distal from the cervical os in a substantially straight line that is parallel to the longitudinal axis of the cervix, and may be an extension of the longitudinal axis of the device, and may comprise sampling in the return direction as well, from the distal to the proximal location. A medical professional may select any particular path desired, and is not limited by this description herein. It may be desired to use a path for sampling that is easily reproducible if multiple samplings over time are intended. For example, a sample is taken at one time point, and a day, a month, a year or more later in time, another representative sample is taken. A representative sample means a sample that has cells from the tissue surface in the area and the cells obtained represent the types and numbers of cells found in the path sampled on the interior surface of the endocervix, so that the cellular constituents present are sampled. A sample that is not a representative sample may provide inaccurate numbers or types of cells which may lead to unnecessary treatments or wrong diagnoses. A method for providing a complete and representative sample comprises providing the sampling area of a device of the present invention at the site of predetermined distance from the cervical os, contacting the inner surface of the endocervix by opening the one or more slits to form the tissue sampling element from the opposing edges of the slit, moving the device in a proximal to distal direction, or distal or proximal direction, or both, along the longitudinal axis of the cervix or an extension of the longitudinal axis of the device so that the tissue sampling element contacts the area of the endocervix defined by that movement in that location and removes at least cells from that area; retaining the removed cells in a sample collection cavity; and removing the device from the subject. The method further comprises removing the sample from the device. The method further comprises examining the sample, for example, to make a diagnosis of the condition of the endocervix of the subject. A device of the present invention comprises a handle, a wand, and a sheath, wherein the wand and sheath form a sample collection cavity, wherein the sheath comprises at least one slit; and wherein the slit comprises at least two opposing edges that when moved apart from each other form a tissue sampling element. The device may comprise an actuator for moving the sheath which moves the at least two opposing edges of a slit apart from each other to form a tissue sampling element. The method further comprises, after obtaining the sample which is retained in the sample collection cavity, closing the slit so that the sample collection cavity is closed and the sample cannot be lost or cannot be contaminated during transit of the device into or out of the subject being sampled.

The present invention comprises a method of collecting a sample from the endocervix of a female, comprising inserting the distal end of a device disclosed herein through the vagina and cervical os of a female to locate a sampling area of the device within the endocervical canal; moving an actuator from a first position to a second position which opens the sample collection cavity and provides opposing edges of at least one slit; contacting the endocervical canal with the opposing edges to acquire a tissue sample; moving the actuator from a second position to a first position; and removing the device from the subject. The method further comprises removing the sample from the device by moving the actuator from a first position to a second position which opens the sample collection cavity, and removing the tissue sample within the sample collection cavity. Alternatively, the method further comprises removing the sampling area of the device by cutting off the distal end of the device or breaking the wand to release a portion of the device comprising the sampling area.

A method of the present invention comprises inserting the distal end of a device disclosed herein, optionally comprising an atraumatic tip, through the vagina and through the cervical os into the endocervical canal. The device is inserted until the indicator passes from sight as it enters the patient and insertion is stopped by the user or the device is physically stopped by a pre-set depth stop located on the outside of the sheath. The actuator is moved from a first position to a second position to move one or more slits to the open position. The entire device or portion of the device is rotated one or more times in a 360 degree motion in one or both directions, clockwise and counterclockwise, or the device is moved longitudinally in a proximal to distal and/or distal to proximal direction, while contacting the inner surfaces of the endocervical canal with the opposing edges of the open slit to obtain tissue samples from the contacted area. Once an adequate sample is collected, the actuator is moved from the second position to the first position to close the slit and to cover and substantially close the sample collection cavity now containing the collected sample. The device is then removed from the patient. The collected sample is treated for histological examination. The sample collection cavity is protected from contamination during insertion and removal of the device into and from the patient, and is open only during sampling within the endocervical canal, and afterwards for release of the collected sample from the device. The closed position of the slit shields the sample collection cavity from contamination upon entry into the endocervical canal and after collection of the sample, protects the collected sample against loss of sample materials, and ectocervical contamination during withdrawal of the sample collection cavity of the device from the endocervical canal and vagina.

An aspect of the present invention comprises a method of collecting a sample wherein the device is inserted one time into the patient. Once the distal end of the device is inserted into the cervical canal of the patient, the sample is collected by rotational or longitudinal movements of the distal end of the device within the cervical canal, and then the device is withdrawn from the patient. In contrast, methods comprising use of currently available devices to obtain a sample often require multiple insertions of the device into the cervical canal. Multiple insertions increase the opportunities for contamination of the sample, or loss of the sample, and increase the discomfort and/or pain felt by the patient. Multiple insertions also increase the variability in the sample collected as it is difficult to sample from the same site on the second and further insertions.

An example of a method of the present invention comprises inserting the distal end of the cervical sample device, optionally comprising an atraumatic tip, through the vagina and through the cervical os into the endocervical canal. The device is inserted until the indicator passes from sight as it enters the patient and insertion is stopped by the user or physically by a pre-set depth stop located on the outside of the sheath. The actuator is rotated from the first position to the second position to move the slit to the open position. The entire device is rotated one or more times in a 360 degree motion in one or both directions, clockwise and counterclockwise, while contacting the inner surfaces of the endocervical canal with the opposing edges of the open slit to obtain tissue samples from the contacted area. Once an adequate sample is collected, the actuator is rotated from the second position to the first position to close the slit and to cover and seal shut the sample collection cavity comprising the collected sample. The device is then removed from the patient. The collected sample is treated for histological examination. The sample collection cavity is protected from contamination during insertion and removal of the device into and from the patient, and is open only during sampling within the endocervical canal, and later for release of the collected sample from the device. The closed position of the slit shields the sample collection cavity from contamination upon entry into the endocervical canal and after collection of the sample, protects the collected sample against loss of sample materials, and ectocervical contamination during withdrawal of the sampling area of the device from the endocervical canal and vagina.

A method of the present invention may comprise dilation of the cervical os to allow insertion of a device of the present invention. Only a small amount of force should be used to insert a device into the cervical canal, and resistance may be found in nulliparous or stenotic os patients. The device is inserted to a depth where the indicator just passes from view of the user or to a pre-set depth stop set by the user or fixed on the outside of the sheath.

A method may further comprise coating at least a portion of the wand and sheath with a surgical lubricant or an anesthetic composition or pain medication, or a treatment composition comprising a therapeutic agent, prior to insertion of the device into a subject. A therapeutic agent may comprise methotrexate, chemotherapeutic compounds, hormones, antibacterial, antimicrobial, antifungal, antiviral, antimycoplasmal, or antiparisital compounds, compounds that reduce inflammation or scar tissue formation, composition comprising one or more antibiotics, antimycoplasma agents, or antiviral compounds; compositions comprising mucoproteins, electrolytes or enzymes, progesterone, estrogen, adrenergic active compounds, noradrenergic active compounds, nonsteroidal anti-inflammatory drug, prostaglandins, other compounds that may treat or prevent conditions related to the endocervix, or combinations thereof.

A method of the present invention comprises insertion of a cervical sampling apparatus so that the slit is positioned in the cervix of a female, which optionally the depth of the slit (which may be one or more slits) within the patient may be indicated by the indicator located on the wand or by a depth stop contacting the outside of the external cervical os of the subject, moving (e.g., rotating) the actuator so that the slit is in an open position; rotating the handle or part of the handle connected to the sheath, and thus the entire apparatus or the sampling part of the apparatus, 360 degrees while the moved apart opposing edges of the open slit, located in the distal end of the sheath, are adjacent to and urged against the interior surfaces of the cervix, and obtaining a sample of the cervical tissue by scraping and/or cutting action of the opposing edges of the slit against the cervical interior surfaces and the cervical tissue is removed to the sample collection cavity. The apparatus may also be moved in a longitudinal direction, proximally to distally and back. Once the one or more 360 degree rotations of the cervical sampling apparatus is accomplished, and the sample is collected, the rotation or movement of the cervical sampling apparatus is stopped, and the actuator is rotated or moved from the first position to a second position so that the slit is moved from an open position to a closed position, and the sample collection cavity is closed. Once the sample collection cavity is closed, the cervical sampling apparatus is withdrawn from the patient. To aid in prevention of contamination of the sample, the exterior of the sheath may be rinsed to remove any adhered tissue or cells. The rinsing solution should not enter the sample collection cavity, but only rinse the exterior surface of the sheath so that cells or tissue acquired during movement of the cervical sampling apparatus to and from the interior of the patient and the sample collected will not be contaminated by, for example, ecto-cervical cells or tissue.

The tissue may be removed from the sample collection cavity by moving the actuator from the first position to a second position so that the slit is moved from the closed position to an open position, and the sample collection cavity is open and the tissue is accessible to be removed. For example, while in a closed position, the distal end of the cervical sampling apparatus, where the sample collection cavity is located, may be immersed in a liquid. The actuator is then rotated from the first position to a second position so that the slit is moved from the closed position to an open position, and the sample collection cavity is open and the tissue may be washed from the sample collection cavity by flowing liquid into and out of the sample collection cavity or by moving the open sample collection cavity within the liquid. The distal tip of the device where the sample collection cavity is located may be submerged into a specimen container with liquid, and with the slit in an open position, the device is swirled or agitated to dislodge the sample. Alternatively, the sample may be retrieved from the sample collection cavity by pipettes, tweezers, graspers, or other instruments, suction, or other methods known to those skilled in the art. In methods disclosed herein, an actuator may be maintained in position 1 and/or position 2 by a locking member.

It is also contemplated that the device may be designed with re-usable components and components that may be removed and discarded. It is contemplated that the removable components would contain the sampling portion of the device and can be assembled or attached on-site. The device may also be designed as a complete single-use but with a detachable segment containing the sampling portion of the device that can be snapped off or otherwise separated from the rest of the device for placement into storage fluids or containers for histological processing. For example, the distal end of the wand, which comprises the reduced diameter section forming the sample collection cavity, may be detachable from the rest of the wand. Additionally, the distal end of the sheath, comprising at least the slit, may also be detachable from the rest of the sheath. For example, at a location proximate to the sample collection cavity and slit, such as a site corresponding to the site of the indicator, the wand may be crimped or have a breakable section. Once the sample is collected and the device is removed from the patient, the distal end of the sheath is cut free from the rest of the sheath, for example by scissors or a scalpel, approximately at the site of the crimped or breakable section of the wand, and force is then used to break the wand at the crimped or breakable section. The released distal end of the wand and sheath, containing the tissue sample, may then be treated in a manner to collect and preserve the tissue sample.

In an aspect, the distal end of a wand comprising the reduced diameter area may be snap-fit or screwed onto a longer segment of wand so as to form a complete assembled wand structure. The longer section of the wand may or may not be attached to a handle of a device. In use, the assembled wand structure is affixed to the handle. A sheath may be of one piece of material or may be perforated in a location to allow the removal of a portion of the sheath. In an aspect, the sheath may be detachable from the actuator. For example, detaching the entire sheath from the actuator, and detaching the distal end of the wand but leaving the wand and the sheath attached to the tip may form a portion of the device that can be used to retrieve or store the collected tissue sample. The tip may also be removable from the wand and or the sheath. In a detached distal section of the device, comprising a tip, a portion of the sheath (or the entire sheath) and a portion of the wand, removal of the tip would allow removal of the sheath portion from the reduced diameter area of the wand so that the tissue sample is easily accessed.

Methods using a device disclosed herein may be used in obtaining tissue samples for diagnosing and prognosing disease, particularly cervical and uterine cancer. A method of the present invention comprising diagnosing disease in a subject comprising providing a device of the present invention to a subject to obtain a sample of endocervical tissue and/or cells that is representative of the types and numbers of cells in a particular location of the endocervix, wherein the sample is reliably obtained, comprising providing the sampling area of a device of the present invention at the site of predetermined distance from the cervical os, contacting the inner surface of the endocervix by opening the one or more slits to form the tissue sampling element from the opposing edges of the slit, contacting the surface of the endocervix with the tissue sample element so that tissue from the surface is removed; retaining the removed cells in a sample collection cavity; and removing the device from the subject. The method further comprises removing the sample from the device. A method comprises using a device as disclosed herein to obtain cells to diagnose cervical lesions, which may be of particular medical significance in diagnosing high grade cervical lesions. A method comprises using a device as disclosed herein to obtain cells to prognose the status of a subject found to have cervical lesions. A method comprises using a device as disclosed herein to monitor the post-surgical status of the endocervix. A method of the present invention comprises using a device as disclosed herein to assess the effectiveness of surgical removal of lesions, such as high-grade cervical lesions. Removing tissue samples using a device of the present invention is not particularly destructive to the endocervical canal and thus sampling with such a device may be performed routinely to monitor a treated area of the cervix. Treatments of the cervix may include surgery (such as loop electrosurgical excision procedure) and may also include monitoring an area after immunotherapies or chemotherapies. Sampling the endocervical canal with a device of the present invention may be used in methods to diagnose or prognose a source of bleeding when the initial symptom is undiagnosed uterine bleeding or preventively after a dilation and curettage procedure. A method of the present invention comprising screening one or more subjects for disease or for abnormal cells in a subject comprising providing a device of the present invention to a subject to obtain a sample of endocervical tissue and/or cells that is representative of the types and numbers of cells in a particular location of the endocervix, wherein the sample is reliably obtained, comprising providing a sampling area of a device of the present invention at the site of predetermined distance from the cervical os, contacting the inner surface of the endocervix by opening the one or more slits to form the tissue sampling element from the opposing edges of the slit, contacting the surface of the endocervix with the tissue sample element so that tissue from the surface is removed; retaining the removed cells in a sample collection cavity; and removing the device from the subject. The method further comprises removing the sample from the device. The method further comprising examining the removed cells to detect cells that are being screened for.

It must be noted that, as used in this specification and the appended claims, the singular forms "a", "an", and "the" include plural referents unless the context clearly dictates otherwise.

All patents, patent applications and references included herein are specifically incorporated by reference in their entireties.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, an aspect includes from the one particular value and/or to the other particular value. Similarly, when values are expressed as approximations, by use of the antecedent "about," it will be understood that the particular value forms an aspect. It will be further understood that the endpoints of each of the ranges are significant both in relation to the other endpoint, and independently of the other endpoint.

The word "or" as used herein means any one member of a particular list and also includes any combination of members of that list.

Diagnostic methods, prognostic methods, screening methods of the present invention may comprise examining a cellular sample or medium by means of an assay, such by an assay known to those of skill in the art, such as an assay comprising nucleic acid detection, biomarker detection, assays comprising an antibody, an affinity-purified polyclonal antibody, or a mAb (monoclonal antibody), and using routine methods, such as immunodetection methods. The assays can be cell-based or cell-free assays. The steps of various useful immunodetection methods have been described in the scientific literature. In the most simple and direct sense, immunoassays are binding assays involving binding between antibodies and antigen. Many types and formats of immunoassays are known and all are suitable for detecting the cells in a sample. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, flow cytometry, protein arrays, multiplexed bead arrays, magnetic capture, in vivo imaging, fluorescence resonance energy transfer (FRET), and fluorescence recovery/localization after photobleaching (FRAP/FLAP). Other detection assays are known to those skilled in the art for determining whether cells from a sample are normal, abnormal, precancerous, cancerous or aplastic cells, as those types of cells are known to those skilled in the art and understood in the scientific and medical literature.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention describe in detail methods, delivery systems, and compositions to occlude the fallopian tubes of human, the present invention is not limited to these embodiments. There are numerous modifications or alterations that may suggest themselves to those skilled in the art for use of the methods, delivery systems, and compositions herein for the occlusion of a variety of conduits in both human and non-human mammals.

The present invention is further illustrated by way of the examples contained herein, which are provided for clarity of understanding. The exemplary embodiments should not to be construed in any way as imposing limitations upon the scope thereof On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

REFERENCES

1. Klam S, Arseneau J, Mansour N, Franco E, Ferenczy A. Comparison of endocervical curettage and endocervical brushing. Obstet Gynecol. 2000; 96:90-94.
2. Andersen W, Frierson H, Barber S, Tabarah S, Taylor P, Underwood P. Sensitivity and specificity of endocervical curettage and the endocervical brush for the evaluation of the endocervical canal. Am J Obstet Gynecol. 1988; 159:702-707. Koss, et al., JAMA. 1989:737.
3. Bidus, et. al., The Clinical Utility of the Diagnostic Endocervical Curettage, 2005.
4. Schiffman, et. al., From Human Papillomarvirus to Cervical Cancer, 2010.
5. Schiffman M and Wentzensen N. From human papillomavirus to cervical cancer. Obstet Gynecol 2010; 116(1): 177-185.
6. National Cancer Institute's SEER Stat Fact Sheets. Cancer: Cervix Uteri. Surveillance Epidemiology and End Results. http://seer.cancer.gov/statfacts/html/cervix.html, August 2012.
7. Saslow D et al. American Cancer Society, American Society for Colposcopy and Cervical Pathology, and American Society for Clinical Pathology screening guidelines for the prevention and early detection of cervical cancer. J Lower Genital Tract Dis 2012; 16(3):175-204.
8. ASCCP (American Society for Colposcopy and Cervical Pathology). Practice Management, Colposcopy. http://www.asccp.org/PracticeManagement/Cervix/Colposcopy, August 2012.
9. Wright T et al. 2006 consensus guidelines for the management of women with abnormal cervical screening tests (by ASCCP). J Lower Genital Tract Dis 2007; 11(4):201-222.
10. Pretorius R et al. Colposcopically directed biopsy, random cervical biopsy, and endocervical curettage in the diagnosis of cervical intraepithelial neoplasia II or worse. Am J Obstet Gynecol 2004; 191:430-434.
11. Bidus M et al. The clinical utility of the diagnostic endocervical curettage. Clin Obstet Gynecol 2005; 45(1): 202-208.
12. Abu J et al. Endocervical curettage at the time of colposcopic assessment of the uterine cervix. Obstet Gynecol Surv 2005; 60(5):315-320.

13. ASCCP (American Society for Colposcopy and Cervical Pathology). Practice Management, Colposcopy: Basic components of the colposcopic exam (Step 12). http://www.asccp.org/PracticeManagement/Cervix/Colposcopy, August 2012.
14. Klam S et al. Comparison of endocervical curettage and endocervical brushing. Obstet Gynecol 2000; 96(1):90-94.
15. Andersen W et al. Sensitivity and specificity of endocervical curettage and the endocervical brush for the evaluation of the endocervical canal. Am J Obstet Gyncol 1988; 159(3):702-707.
16. Driggers R and Zahn C. To ECC or not to ECC: the question remains. Obstet Gyncol Clin N Am 2008; 35:583-597.
17. Moniak C et al. Endocervical curettage in evaluating abnormal cervical cytology. Obstet Gynecol Surv 2000; 55(8):487-489. Abstract only.
18. Gage J et al. Number of cervical biopsies and sensitivity of colposcopy. Obstet Gynecol 2006; 108(2);264-272.
19. Moniak C et al. Endocervical curettage in evaluating abnormal cervical cytology. J Reprod Med. 2000; 45(4): 285-92.
20. Helmerhorst T. Clinical significance of endocervical curettage as part of colposcopic evaluation. A review. Int J Gynecol Cancer 1992; 2:256-262.
21. Solomon D. Diagnostic utility of endocervical curettage in women undergoing colposcopy for equivocal or low-grade colposcopy cytologic abnormalities. Obstet Gynecol 2007; 110(2/1):288-295.
22. Boardman et al. A randomized trial of the sleeved cytobrush and the endocervical curette. Obstet Gynecol 2003; 101(3):426-430.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, dimensions, etc.), but some errors and deviations should be accounted for. Unless indicated otherwise, parts are parts by weight, temperature is in ° C. or is at ambient temperature, and pressure is at or near atmospheric.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Example 1

Sheath Collecting Cervical Sampling System

Two cervical sampling systems were designed having two sample collecting cavity configurations with slits having 1) a spiral (or helical) cut and 2) a straight cut. The spiral cut slit is shown in FIG. 4 and the straight cut slit is shown in FIG. 5. The devices were used to collect a tissue sample in a simulated endocervical canal. This study used a gelatin tissue phantom (Vyse Ballistic gelatin (prepared at 10% gelatin in water) to mimic the endocervical canal, as the gelatin is a type and composition used to mimic human body tissue. The 10% gelatin models were prepared using the following: 726 g water, 80.7 g gelatin, 6 drops foam eater, and 11 drops cinnamon oil. The endocervical canal was created using a 2 mm diameter tube as a mold. While the gelatin was still liquid, the 2 mm tube was inserted into the gelatin to create the endocervical canal. After the gelatin had cooled and solidified, the tubes were removed leaving a hollow simulated endocervical canal.

Each device was constructed of an outer sheath with either a spiral or straight cut slit. The sample collecting cavity was overlaid by the sheath and closed by one of more slits, each having a length of approximately 1.5 cm. The spiral slit 441 had either one or two complete revolutions in the 1.5 cm long section while the straight cut slit was four slits, 541, 542, 543 and 544, evenly spaced apart and parallel to the longitudinal axis of the sheath, and each slit ran from a site proximate the tip 460 for a length of approximately 1.5 cm. The distal end of the sheath was affixed to the tip 460/560 of the wand 420/520 using cyanoacrylate adhesive. The proximal end of the sheath was affixed to an actuator, in this case a sheath nut 430/530. The wand 420/520 was prepared beforehand so that the section beneath the sampling area (below where the slit(s) is located) had a reduced diameter, made by grinding the wand in that distal region to approximately 2 mm in diameter. The wand 420/520 is affixed on its proximal end to a handle 410/510. The circled area A FIG. 5A, is enlarged to show detail in FIGS. 5B and C. The wand is not shown inside the sheath in the figures, except in FIG. 5C to show the reduced diameter section. The indicator 180 is shown.

Each device was inserted into a gelatin tissue phantom and evaluated for being able to remove gelatin from the simulated endocervical canal. For the spiral cut design, the device was operated by holding the wand 420 in place while moving the sheath by rotating the sheath nut 430, which caused the opposing edges of slit 441 to move apart from each other and open the sample collecting cavity. For the straight cut design, the device was operated by holding the wand 420 steady and unmoving while pushing the outer sheath forward by sliding the sheath nut 430 in a distal direction down the wand 420. Moving the sheath nut from its first position to a second position distally displaced from the first position caused the sample collecting cavity to be open by causing the opposing edges of the slit to be displaced and moved apart from contacting each other. Once in the open position, a locking mechanism 480 held the sheath nut immobile so that the sample collecting cavity remained open. Each device was then rotated in the gelatin phantom clockwise one complete revolution and then counter-clockwise one complete revolution. For the spiral cut design, the sheath nut 430 was then rotated to the first position to close the sample collecting cavity by moving the opposing edges of the slit so as to be adjacent once again. For the straight cut design, the sheath nut was then moved in a proximal direction to its original location, the first position, which caused the sheath to lengthen and caused the opposing edges of the slits to be adjacent to one another, and in a closed position. Each device was removed from the test model and the amount of gelatin collected was evaluated. The number of cut revolutions was tested, as was the type of materials used in the sheath and wand.

The following device prototypes were prepared for testing:

| Device ID | Sheath Material | Spiral or Straight Cut | Spiral Cut # Revolutions or # of Slits for Straight cut | Wand Material |
|---|---|---|---|---|
| A | PEEK | Spiral | 2 | Stainless Steel |
| B | PEEK | Spiral | 1 | Stainless Steel |
| C | Polycarbonate | Spiral | 2 | Plastic Rod |
| D | LDPE | Spiral | 2 | Plastic Rod |
| E | LDPE | Spiral | 1 | Plastic Rod |
| F | PEEK | Straight | 4 | Stainless Steel |

Each device was tested in a new endocervical gelatin tissue phantom and the following results were collected:

| Device ID | Closed Sheath OD (mm) | Open Sheath OD (mm) | Amount Gelatin Collected (g) (n = 1) | Comments |
|---|---|---|---|---|
| A | 3.5 | 5.3 | 0.051 | Visible Material present |
| B | 3.3 | 5.5 | 0.035 | Visible Material present |
| C | 3.2 | 4.8 | 0.020 | Visible Material present |
| D | 3.6 | 6.2 | 0.032 | Visible Material present |
| E | 3.6 | 4.5 | 0.01 | Visible Material present |
| F | 3.4 | 6.7 | 0.060 | Visible Material present. Device could be opened to a larger diameter than all other devices. Removal of material was easiest with this device. |

All devices tested in this study removed simulated tissue material from the simulated endocervical canal.

Example 2

Handheld Cervical Cell and Tissue Sampling Device

A handheld device (overall length 11¾") was constructed comprising a stainless steel shaft (length 7¼" extending past sheath nut) machined to include a reduced diameter area for sample collection and the shaft tip (diameter 0.145"), a polycarbonate sheath (outer diameter 0.145" and inner diameter 0.125") with a spiral cut section (length 2 cm) created using a laser cutting process, a sheath nut, a locking knob and a handle (length 4"). The components were assembled as generally shown in FIG. 4.

The handheld cervical cell and tissue sampling was designed to capture an adequate volume of sample from the targeted area with a single entry/pass into the patient. The shaft tip in one aspect was tapered to provide for ease of entry and dilation. When passed into the cervical canal, the sample collecting cavity was protected from contamination when the slit was in the closed position. One aspect of the device incorporated a marker band (not shown) that was used to ensure proper depth placement into the cervical canal. Once the device was properly introduced, the spiral cut slit of the sheath, which contains laser cut edges was opened, the walls of the cervical canal were contacted to capture a complete circumferential sample by rotating the handle 360 degrees in each direction, clockwise and counterclockwise. The sample was collected within the sheath in the sample collecting cavity and was protected from contamination when the sheath was closed during withdrawal from the patient.

Other aspects of the device included a locking knob that was rotated to lock or free the sheath nut and allowed the sheath nut to turn. The sheath nut was turned to move the slit, to expand or open the slit, and had markings indicating when the slit is in the "open" or "closed" position. Once in the "open" position, the locking knob is rotated (tightened) to lock the sheath nut and thus the slit in position during use. Once the slit is moved to the open position and the sheath nut locked, the entire device is rotated counter clockwise one time and clockwise one time, rotating 360 degrees in each direction. The locking knob was loosened and then the sheath nut was turned to close the slit before removing the distal end of the device from the cervical canal.

The handheld sampling device was tested ex vivo in a patient's cervical canal following a planned hysterectomy with removal of the uterus with intact cervix. The patient was a 34 year old multiparous female (gravidity=6, parity=4, with 4 C-section deliveries). The device was inserted into endocervical canal with the locking knob facing up. The locking knob was rotated to release the sheath nut. The sheath nut, which was connected to sheath, was rotated to the right until the black mark on the sheath nut was facing up (position 2) and the slit was fully opened. The sheath nut was locked in position 2 by turning the locking knob. The device was rotated one complete revolution clockwise and then one complete revolution counterclockwise. The locking knob was turned to release the sheath nut. The sheath nut was rotated to position 1 to close the slit. The device was removed from the endocervical canal. The locking knob was rotated to release the sheath nut and the slit was opened by rotating the sheath nut to position 2. The device tip was placed in formalin to remove the sample for processing, where it was analyzed by the Pathology Department.

The results from the pathology analysis are as follows:
Ectocervical Tissue: 0%
Endocervical Tissue: 100%
Endometrial Tissue: 0%
Sample Amount: Approximately 1.0-cm in aggregate The sample was deemed adequate for making a pathological diagnosis and the pathologist remarked that the specimen consisted of benign endocervical mucosa with mild chronic inflammation. The results of the pathological analysis indicated that the device performed optimally as no ectocervical or endometrial tissue was collected and a pathological diagnosis could be made from the sample taken.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A method of obtaining an endocervical sample, comprising:
   a) introducing into the endocervical canal of a female animal at least a portion of a helical slit in a distal portion of a cervical sampling apparatus comprising,
      i. a handle having a distal end and a longitudinal axis;
      ii. an elongate wand extending outwardly from the distal end of the handle substantially along the longitudinal axis, wherein the wand has an exterior surface, a front end that defines a conical tip having a proximal and a distal end, and a back end, wherein the back end is fixedly mounted to the distal end of the handle;
iii. a selectively moveable actuator coupled to the handle and to a proximal end of a sheath; wherein the sheath encapsulates a portion of the wand and is fixedly mounted to the proximal end of the tip, and to a portion of an actuator, wherein the slit is located in a distal portion of the sheath and is selectively movable between a closed position, in which opposing edges of the helical slit substantially adjoin, and an open position, in which the opposing edges of the slit are spaced from each other; and wherein the actuator is selectively movable between a first position, in which the slit is positioned in the closed position, and a second position, in which the helical slit is positioned in the open position;
b) moving the actuator to the second position to selectively move the slit to the open position;
c) selectively urging the open positioned slit against tissue in the endocervical cavity, while simultaneously rotating the handle of the cervical sampling apparatus to affect corresponding rotation of the open positioned slit, to collect tissue and cells into a sample collection cavity;
d) moving the actuator to the first position to selectively move the slit to the closed position to selectively close the sample collection cavity; and
e) withdrawing the cervical sampling apparatus from the subject.

2. The method of claim 1, wherein the step of rotating the handle of the cervical sampling apparatus includes rotating the handle at least one complete revolution in a clockwise or counterclockwise direction.

3. The method of claim 1, wherein the method is performed to obtain cells for diagnosing cervical lesions.

4. The method of claim 1, wherein the method is performed to monitor the post-surgical status of the endocervix and the effectiveness of surgical removal of cervical lesions.

5. The method of claim 1, wherein the method is performed to diagnose cervical sources of undiagnosed bleeding.

6. A cervical sampling apparatus, comprising:
a) a handle having a distal end and a longitudinal axis;
b) an elongate wand extending outwardly from the distal end of the handle substantially along the longitudinal axis, wherein the wand has an exterior surface, a front end that defines a conical tip having a proximal and a distal end, and a back end, and wherein the back end is fixedly mounted to the distal end of the handle;
c) a selectively moveable actuator coupled to the distal end of the handle and to a proximal end of a sheath;
d) a selectively moveable actuator coupled to the handle and to a proximal end of the sheath, wherein the sheath encapsulates a portion of the wand and is fixedly mounted to the proximal end of the tip, a and to a portion of the actuator, wherein the sheath defines a helical slit that is located in a distal end portion of the sheath, and is selectively movable between a closed position, in which opposing edges of the slit substantially adjoin, and an open position, in which the opposing edges of the slit, and wherein the actuator is selectively movable between a first position, in which the slit is positioned in the closed position, and a second position, in which the helical slit is positioned in the open position,
wherein the distal end portion of the sheath and a portion of the exterior surface of the wand underlying the distal end portion of the sheath define a sample collection cavity.

7. The apparatus of claim 6, wherein the slit is selectively movable between a closed position, in which the opposing edges of the slit substantially adjoin to substantially seal the sample collection cavity, and an open position, in which the opposing edges of the slit are spaced from each other for obtaining a tissue or cell sample when positioned within an endocervical cavity.

8. The apparatus of claim 6, wherein the conical tip defines an atraumatic tip.

9. A method of diagnosing endocervical cancer, comprising:
a) introducing into the endocervical canal of a female animal at least a portion of a helical slit in a distal portion of a cervical sampling apparatus comprising,
i. a handle having a distal end and a longitudinal axis;
ii. an elongate wand extending outwardly from the distal end of the handle substantially along the longitudinal axis, wherein the wand has an exterior surface, a front end that defines a conical tip having a proximal and a distal end, and a back end, wherein the back end is fixedly mounted to the distal end of the handle;
iii. a selectively moveable actuator coupled to the handle and to a proximal end of a sheath; wherein the sheath encapsulates a portion of the wand and is fixedly mounted to the proximal end of the tip, and to a portion of an actuator, wherein the slit is located in a distal portion of the sheath and is selectively movable between a closed position, in which opposing edges of the helical slit substantially adjoin, and an open position, in which the opposing edges of the slit are spaced from each other; and wherein the actuator is selectively movable between a first position, in which the slit is positioned in the closed position, and a second position, in which the helical slit is positioned in the open position;
b) moving the actuator to the second position to selectively move the slit to the open position;
c) selectively urging the open positioned slit against tissue in the endocervical cavity, while simultaneously rotating the handle of the cervical sampling apparatus to affect corresponding rotation of the open positioned slit, to collect tissue and cells into a sample collection cavity underlying the open position slit;
d) moving the actuator to the first position to selectively move the slit to the closed position to selectively close the sample collection cavity;
e) withdrawing the cervical sampling apparatus from the subject.
f) examining the collected tissue and/or cells for aplastic or abnormal cells, wherein the presence of aplastic or abnormal cells indicates a diagnosis of cancer.

10. The method of claim 9, wherein the step of rotating the handle of the cervical sampling apparatus includes rotating the handle at least one rotation in a clockwise direction and one rotation in a counterclockwise location.

* * * * *